(12) United States Patent
Nakafuji et al.

(10) Patent No.: US 10,146,131 B2
(45) Date of Patent: Dec. 4, 2018

(54) COMPOSITION, METHOD FOR PRODUCING PATTERNED SUBSTRATE, FILM AND FORMING METHOD THEREOF, AND COMPOUND

(71) Applicant: JSR CORPORATION, Tokyo (JP)

(72) Inventors: Shin-ya Nakafuji, Tokyo (JP); Fumihiro Toyokawa, Tokyo (JP); Gouji Wakamatsu, Tokyo (JP); Yoshio Takimoto, Tokyo (JP); Katsuhisa Mizoguchi, Tokyo (JP); Takashi Okada, Tokyo (JP); Takaaki Uno, Tokyo (JP); Takeshi Endo, Iizuka-shi (JP); Masaki Moritsugu, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/862,352

(22) Filed: Sep. 23, 2015

(65) Prior Publication Data

US 2016/0011512 A1    Jan. 14, 2016

Related U.S. Application Data

(63) Continuation of application No. PCT/JP2014/057626, filed on Mar. 19, 2014.

(30) Foreign Application Priority Data

Mar. 29, 2013 (JP) .................. 2013-075304
Mar. 29, 2013 (JP) .................. 2013-075323

(51) Int. Cl.
    *G03F 7/11*       (2006.01)
    *C07D 493/10*     (2006.01)
    *C08G 65/40*      (2006.01)
    *C07C 255/54*     (2006.01)
    *C08G 65/38*      (2006.01)
    *C09D 171/00*     (2006.01)
    *G03F 7/16*       (2006.01)
    *G03F 7/36*       (2006.01)
    *H01L 21/02*      (2006.01)
    *C09D 171/10*     (2006.01)
    *G03F 7/09*       (2006.01)

(52) U.S. Cl.
    CPC .............. *G03F 7/11* (2013.01); *C07C 255/54* (2013.01); *C07D 493/10* (2013.01); *C08G 65/38* (2013.01); *C08G 65/40* (2013.01); *C09D 171/00* (2013.01); *C09D 171/10* (2013.01); *G03F 7/094* (2013.01); *G03F 7/16* (2013.01); *G03F 7/36* (2013.01); *H01L 21/02118* (2013.01)

(58) Field of Classification Search
    CPC ....... G03F 7/11; C07C 255/51; C07C 255/54; C08G 65/38; C08G 65/40
    See application file for complete search history.

(56) References Cited

U.S. PATENT DOCUMENTS

2012/0046503 A1    2/2012 Priske et al.

FOREIGN PATENT DOCUMENTS

| JP | H02-199121 A | 8/1990 |
|----|--------------|--------|
| JP | H02-247222 A | 10/1990 |
| JP | H02-276822 A | 11/1990 |
| JP | H03-162413 A | 7/1991 |
| JP | H04-233939 A | 8/1992 |
| JP | H04-236223 A | 8/1992 |
| JP | H05-140296 A | 6/1993 |
| JP | H05-238990 A | 9/1993 |
| JP | H05-339365 A | 12/1993 |
| JP | 2000-159715 A | 6/2000 |
| JP | 2002-356551 A | 12/2002 |
| JP | 2004-168748 A | 6/2004 |
| JP | 2004-177668 A | 6/2004 |
| JP | 2005-128509 A | 5/2005 |

(Continued)

OTHER PUBLICATIONS

STIC search, Jul. 10, 2018 (Year: 2018).*

(Continued)

*Primary Examiner* — Melvin C. Mayes
*Assistant Examiner* — Stefanie J Cohen
(74) *Attorney, Agent, or Firm* — Oblon, McClelland, Maier & Neustadt, L.L.P.

(57) ABSTRACT

A composition includes a compound including a partial structure represented by formula (1), and solvent. In the formula (1), $X^1$ and $X^2$ each independently represent a substituted or unsubstituted ring structure having 4 to 10 ring atoms constituted taken together with the spiro carbon atom and the carbon atoms of the aromatic ring adjacent to $X^1$ or $X^2$; n1 and n2 are each independently an integer of 0 to 2; and the sum of k1 and k2 are each independently an integer of 1 to 8, wherein the sum of k1 and k2 is no less than 2 and no greater than 16. The compound is preferably represented by formula (2). The sum of k1 and k2 in the formula (1) is preferably no less than 3.

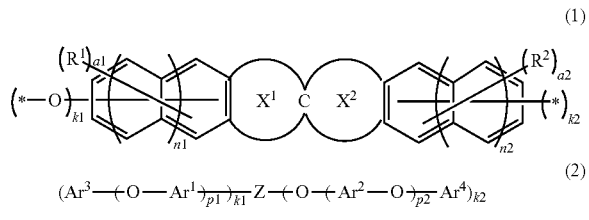

21 Claims, No Drawings

(56) References Cited

FOREIGN PATENT DOCUMENTS

| JP | 2006-058427 A | 3/2006 |
|---|---|---|
| JP | 2006-063236 A | 3/2006 |
| JP | 2011-526828 A | 10/2011 |
| JP | 2012-519061 A | 8/2012 |
| TW | I310048 B | 5/2009 |
| WO | WO 2010/002404 A1 | 1/2010 |

OTHER PUBLICATIONS

Qun-Sheng Guo, et al., "A facile synthesis of 3 or 3,3'-substituted binaphthols and their applications in the asymmetric addition of diethylzinc to aldehydes", Journal of Organometallic Chemistry, 2006, vol. 691, pp. 1282-1287.

Yasmeen Badar, et al., "Optical Activity in the 1,1'-Binaphthyl Series. Optically Active 8,8'-Dimethyl-1,1'-binaphthyl", Journal of the Chemical Society, 1965, pp. 1412-1418.

Jen-Chieh Hsieh, et al., "O-Dihaloarenes as aryne precursors for nickel-catalyzed [2+2+2] cycloaddition with alkynes and nitriles", Chemical Communications, 2008, pp. 2992-2994.

R. G. R. Bacon, et al., "Cyclisations with Hydrazine. Part III. Syntheses of Pentaphene and Dinaphtho[2,1-d : 1',2'-f][1,2]diazocine", Journal of the Chemical Society, 1963, pp. 839-845.

Katsuhisa Mizoguchi, et al., "Negative-Working Photosensitive Poly(phenylene ether) Based on Poly(2,6-dimethyl-1,4-phenylene ether), a Cross-Linker, and a Photoacid Generator", Macromolecules, 2010, vol. 43, pp. 2832-2839.

Katsuhisa Mizoguchi, et al., "Direct Patterning of Poly(ether ether sulfone) Using a Cross-linker and a Photoacid Generator", Polymer Journal, 2008, vol. 40, No. 7, pp. 645-650.

Katsuhisa Mizoguchi, et al., "Negative-Type Photosensitive Poly(phenylene ether) Based on Poly(2,6-dimethyl-1,4-phenylene ether), a Crosslinker, and a Photoacid Generator", Journal of Polymer Science: Part A, 2008, vol. 46, pp. 4949-4958.

International Search Report dated Jun. 24, 2014 in PCT/JP2014/057626 filed Mar. 19, 2014 (w/ English translation).

Office Action dated Mar. 15, 2017, in Taiwanese Patent Application No. 103111494 (w/ English translation).

Office Action dated Jul. 11, 2017, in Japanese Patent Application No. 2015-508390 (w/ English translation).

* cited by examiner

COMPOSITION, METHOD FOR PRODUCING PATTERNED SUBSTRATE, FILM AND FORMING METHOD THEREOF, AND COMPOUND

CROSS-REFERENCE TO RELATED APPLICATIONS

The present application is a continuation application of International Application No. PCT/JP2014/057626, filed Mar. 19, 2014, which claims priority to Japanese Patent Application No. 2013-075304, filed Mar. 29, 2013, and to Japanese Patent Application No. 2013-075323, filed Mar. 29, 2013. The contents of these applications are incorporated herein by reference in their entirety.

BACKGROUND OF THE INVENTION

Field of the Invention

The present invention relates to a composition, a production method of a patterned substrate, a film and a forming method thereof, and a compound.

Discussion of the Background

In manufacturing semiconductor devices, multilayer resist processes have been employed for attaining a high degree of integration. In these processes, a composition for forming a resist underlayer film is first coated on a substrate to provide a resist underlayer film, and then a resist composition is coated on the resist underlayer film to provide a resist film. Thereafter, the resist film is exposed through a mask pattern or the like, and developed with an appropriate developer solution to form a resist pattern. Subsequently, the resist underlayer film is dry-etched using the resist pattern as a mask, and further the substrate is dry-etched using the resultant resist underlayer film pattern as a mask, thereby enabling a desired pattern to be formed on the substrate. Resist underlayer films used in such multilayer resist processes are required to exhibit general characteristics such as optical characteristics, e.g., the refractive index and the extinction coefficient, as well as etching resistance.

In recent years, in order to further increase the degree of integration, microfabrication of patterns has been further in progress. Also in connection with the multilayer resist processes described above, various characteristics as in the following are demanded for resist underlayer films formed, as well as compositions for forming the same. To meet these demands, structures of polymers, etc., contained in the composition, and functional groups included in the polymers have been variously investigated (see Japanese Unexamined Patent Application, Publication No. 2004-177668).

Moreover, the multilayer resist processes involving a procedure of forming a hard mask as an intermediate layer on the resist underlayer film has been contemplated recently. Specifically, since an inorganic hard mask is formed on a resist underlayer film using CVD techniques according to this procedure, particularly in a case where a nitride inorganic hard mask is formed, the temperature is elevated to be as high as at least 300° C. and typically no less than 400° C., and thus, the resist underlayer film is required to have superior heat resistance.

Still further, patterns are more frequently formed recently on a substrate having a plurality of types of trenches, particularly trenches having aspect ratios that differ from each other, the resist underlayer film formed is desired to have these trenches sufficiently embedded thereinto, and also have superior flatness.

SUMMARY OF THE INVENTION

According to one aspect of the present invention, a composition includes a compound including a partial structure represented by formula (1), and a solvent.

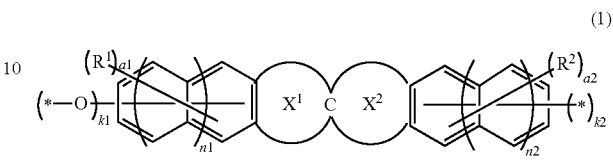

In the formula (1), $X^1$ and $X^2$ each independently represent a substituted or unsubstituted ring structure having 4 to 10 ring atoms constituted taken together with the spiro carbon atom and the carbon atoms of the aromatic ring adjacent to $X^1$ or $X^2$; $R^1$ and $R^2$ each independently represent a halogen atom, a nitro group or a monovalent organic group; a1 and a2 are each independently an integer of 0 to 7, wherein in a case where $R^1$ and $R^2$ are each present in a plurality of number, the plurality of $R^1$s are each identical or different, and the plurality of $R^2$s are each identical or different; n1 and n2 are each independently an integer of 0 to 2; k1 and k2 are each independently an integer of 1 to 8, wherein a sum of k1 and k2 is no less than 2 and no greater than 16, and a sum of a1 and k1, and a sum of a2 and k2 are each no less than 1 and no greater than 8; and * represents an atomic bonding.

According to another aspect of the present invention, a film is formed from the composition.

According to further aspect of the present invention, a method for producing a patterned substrate, includes applying the composition on an upper face side of a substrate to provide a resist underlayer film. A resist pattern is formed directly or indirectly on the resist underlayer film. At least the resist underlayer film and the substrate are etched using the resist pattern as a mask such that the substrate has a pattern.

According to further aspect of the present invention, a method for forming a film, includes providing a coating film using the composition, and removing the solvent from the coating film.

According to further aspect of the present invention, a compound includes a partial structure represented by formula (1).

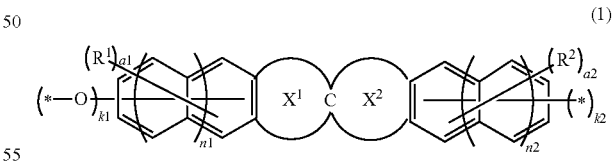

In the formula (1), $X^1$ and $X^2$ each independently represent a substituted or unsubstituted ring structure having 4 to 10 ring atoms constituted taken together with the Spiro carbon atom and the carbon atoms of the aromatic ring adjacent to $X^1$ or $X^2$; $R^1$ and $R^2$ each independently represent a halogen atom, a nitro group or a monovalent organic group; a1 and a2 are each independently an integer of 0 to 7, wherein in a case where $R^1$ and $R^2$ are each present in a plurality of number, the plurality of $R^1$s are each identical or different, and the plurality of $R^2$s are each identical or different; n1 and n2 are each independently an integer of 0 to 2; k1 and k2 are each each independently an integer of 1 to 8, wherein a sum of k1 and k2 is no less than 2 and no greater than 16, and a sum of a1 and k1, and a sum of a2 and k2 are each no less than 1 and no greater than 8; and * represents an atomic bonding.

DESCRIPTION OF THE EMBODIMENTS

According to an embodiment of the invention made for solving the aforementioned problems, a composition contains:

a compound having a partial structure represented by the following formula (1) (hereinafter, may be also referred to as "partial structure (I)") (hereinafter, may be also referred to as "(A) compound" or "compound (A)"); and a solvent (hereinafter, may be also referred to as "(B) solvent" or "solvent (B)"),

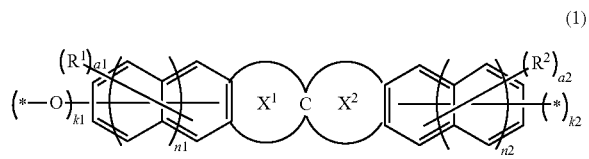

wherein, in the formula (1), $X^1$ and $X^2$ each independently represent a substituted or unsubstituted ring structure having 4 to 10 ring atoms constituted taken together with a spiro carbon atom and the carbon atoms of an aromatic ring; $R^1$ and $R^2$ each independently represent a halogen atom, a nitro group or a monovalent organic group; a1 and a2 are each independently an integer of 0 to 7, wherein in a case where $R^1$ and $R^2$ are each present in a plurality of number, the plurality of $R^1$s are each identical or different, and the plurality of $R^2$s are each identical or different; n1 and n2 are each independently an integer of 0 to 2; k1 and k2 are each independently an integer of 1 to 8, wherein the sum of k1 and k2 is no less than 2 and no greater than 16, and the sum of a1 and k1, and the sum of a2 and k2 are each no less than 1 and no greater than 8; and * represents an atomic bonding.

The film according to another embodiment of the present invention is formed from the composition described above.

The method for producing a patterned substrate according to still another embodiment of the present invention includes the steps of:

forming a resist underlayer film on the upper face side of a substrate;

forming a resist pattern directly or indirectly on the resist underlayer film; and etching at least the resist underlayer film and the substrate using the resist pattern as a mask such that the substrate has a pattern, in which the resist underlayer film is formed from the composition.

The method for forming a film according to yet another embodiment of the present invention includes the steps of:

providing a coating film; and removing a solvent from the coating film, wherein the coating film is formed from the composition described above.

The compound according to other embodiment of the present invention has the partial structure represented by the above formula (1).

The film according to still other embodiment of the present invention includes the compound described above.

In the composition according to the embodiment of the present invention, PGMEA may be used as a solvent, and the composition is capable of forming a film that is superior in heat resistance and flatness while general characteristics such as etching resistance are maintained. The method for producing a patterned substrate according to still another embodiment of the present invention enables a resist underlayer film that is superior in heat resistance and flatness to be readily formed owing to superior coating properties, and in turn enables a favorable pattern to be formed. The film according to another embodiment of the present invention is superior in both optical characteristics such as transparency, and thermal characteristics such as heat resistance. The method for forming a film according to yet another embodiment of the present invention enables the film of the another embodiment of the present invention described above to be readily formed. The compound according to other embodiment of the present invention can be suitably used as a component of the composition of the embodiment of the present invention described above. Therefore, these can be suitably used, for example, for manufacture of semiconductor devices and the like in which further progress of miniaturization is expected in the future. Hereinafter, embodiments of the present invention will be described in detail.

Composition

The composition contains (A) a compound and (B) a solvent. The composition may contain as a favorable component, (C) an acid generating agent and (D) a crosslinking agent, and may also contain other optional component within a range not leading to impairment of the effects of the present invention. Hereinafter, each component will be explained.

(A) Compound

The compound (A) has the partial structure (I). Since the composition contains the compound (A), PGMEA may be used as a solvent, and formation of a film that is superior in heat resistance and flatness is enabled while general characteristics such as etching resistance are maintained. Although the reason for achieving the described above effects owing to the composition having the aforementioned constitution is not necessarily clear, for example, the reason may be inferred as follows. The compound (A) has the partial structure (I), and this partial structure (I) has a specific structure as represented by the above formula (1), in which the ring structures $X^1$ and $X^2$ sharing a spiro carbon atom are each fused with the aromatic ring. The film formed from the composition is believed to achieve the superior heat resistance resulting from this specific structure. Moreover, the composition for forming a resist underlayer film has an adequately low viscosity. As a result, the composition can be suitably used as a coatable underlayer material, enables trenches to be sufficiently embedded, and also enables a resist underlayer film that is superior in flatness to be formed. Furthermore, in a case where the sum of k1 and k2 in the following formula (1) is no less than 3, the partial structure (I) serves as a branching point. Owing to this branching point, the compound (A) loses planarity, whereby the interactions between molecules are weakened, leading to an increase of the solubility in a poorly polar solvent such as PGMEA.

Partial Structure (I)

The partial structure (I) is represented by the following formula (I).

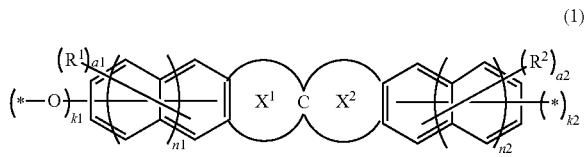

(1)

In the above formula (1), $X^1$ and $X^2$ each independently represent a substituted or unsubstituted ring structure having 4 to 10 ring atoms constituted taken together with a Spiro carbon atom and the carbon atoms of an aromatic ring; $R^1$ and $R^2$ each independently represent a halogen atom, a nitro group or a monovalent organic group; a1 and a2 are each independently an integer of 0 to 7, wherein in a case where $R^1$ and $R^2$ are each present in a plurality of number, the plurality of $R^1$s are each identical or different, and the plurality of $R^2$s are each identical or different; n1 and n2 are each independently an integer of 0 to 2; and k1 and k2 are each independently an integer of 1 to 8, wherein the sum of k1 and k2 is no less than 2 and no greater than 16, and the sum of a1 and k1, and the sum of a2 and k2 are each no less than 1 and no greater than 8; and * represents an atomic bonding.

The ring structures represented by $X^1$ and $X^2$ are not particularly limited as long as they have the structure described above, and may be: an alicyclic structure; a ring structure having a double bond between ring-constructing carbon atoms; or a ring structure containing a part of an aromatic ring other than the aromatic ring represented in the above formula (1), and these may include a hetero atom other than the carbon atom as a ring-constructing atom, or may have a substituent binding to the ring-constructing atom. Also, the ring structures represented by $X^1$ and $X^2$ may be the same or different, and in light of the heat resistance and the like of the film formed from the composition, and in light of ease in synthesis of the compound that provides the partial structure (I), the ring structures represented by $X^1$ and $X^2$ are preferably the same.

The ring atoms of the ring structure is, in light of the heat resistance and the like of the film formed from the composition, preferably no less than 4 and no greater than 8, more preferably 5 or 6, and still more preferably 5.

Examples of the substituent that the ring structure may have include
  monovalent substituents e.g.:
  hydrocarbon groups including chain hydrocarbon groups exemplified by alkyl groups such as a methyl group, an ethyl group, a propyl group and a butyl group, alkenyl groups such as an ethenyl group and a propenyl group, and alkynyl groups such as anethynyl group and a propynyl group;
  alicyclic hydrocarbon groups exemplified by cycloalkyl groups such as a cyclopropyl group, a cyclobutyl group, a cyclopentyl group, a cyclohexyl group, a norbornyl group and an adamantyl group, and cycloalkenyl groups such as a cyclopentenyl group, a cyclohexenyl group and a norbornenyl group; and
  aromatic hydrocarbon groups exemplified by aryl groups such as a phenyl group, a tolyl group, a xylyl group, a naphthyl group and an anthryl group, aralkyl groups such as a benzyl group, a phenethyl group and a naphthylmethyl group;
  oxyhydrocarbon groups such as a methoxy group, an ethoxy group, a propoxy group, a phenoxy group and a naphthyloxy group;
  carbonyloxy hydrocarbon groups such as a methoxycarbonyl group and a phenoxycarbonyl group;
  acyl groups such as a formyl group, an acetyl group, a propionyl group and a benzoyl group;
  acyloxy groups such as an acetyloxy group, a propionyloxy group and a benzoyloxy group;
  halogen atoms such as a fluorine atom, a chlorine atom, a bromine atom and an iodine atom;
  a cyano group, a nitro group and a formyl group, and the like,
  divalent substituents e.g.:
  hydrocarbon groups including chain hydrocarbon groups such as a methylidene group, an ethylidene group and a propylidene group;
  alicyclic hydrocarbon groups such as a cyclopropylidene group, a cyclobutylidene group, a cyclopentylidene group, a cyclohexylidene group and a norbornylidene group; and
  aromatic hydrocarbon groups such as a benzylidene group, a phenethylidene group, a naphthylmethylidene group and a fluorenylidene group;
  keto groups (=O), and the like.

Among these substituents, the monovalent substituent is preferably a hydrocarbon group, more preferably a chain hydrocarbon group or an aromatic hydrocarbon group, still more preferably an alkyl group or an aryl group, particularly preferably a methyl group, an ethyl group or a phenyl group, and further particularly preferably a methyl group.

The divalent substituent is preferably a hydrocarbon group or a keto group, more preferably an aromatic hydrocarbon group or a keto group, and still more preferably a fluorenylidene group or a keto group.

Examples of the hetero atom which may be included in the ring structure include an oxygen atom, a nitrogen atom, a sulfur atom, and the like. Of these, in light of the heat resistance and the like of the film formed from the composition, an oxygen atom is preferred. The number of the hetero atom which may be included in the ring structure is preferably 1 or 2, and more preferably 1.

The ring structure represented by $X^1$ and $X^2$ is exemplified by ring structures represented by the following formulae (1-1) to (1-3), and the like.

(1-1)

(1-2)

(1-3)

In the above formulae (1-1) to (1-3), $R^a$ represents a Spiro carbon atom shared by both the ring structures of $X^1$ and $X^2$; $R^b$ and $R^c$ represent two carbon atoms shared by the aromatic ring and the ring structures of $X^1$ or $X^2$; $R^A$ represents a monovalent group that substitutes for a hydrogen atom binding to the carbon atom constructing the ring structure, or a divalent group constructed taken together by these groups together with the carbon atom to which these bond, wherein in a case where $R^4$ is present in a plurality of number, the plurality of $R^4$s may be the same or different.

In the above formula (1-1), p1 and p2 are each independently an integer of 0 to 4, wherein the sum of p1 and p2 is no less than 1 and no greater than 7; and s1 is an integer of 0 to 14.

In the above formula (1-2), q1, q2 and q3 are each independently, an integer of 0 to 4, wherein the sum of q1, q2 and q3 is no less than 0 and no greater than 5; and s2 is an integer of 0 to 14.

In the above formula (1-3), r1, r2 and r3 are each independently an integer of 0 to 4, wherein the sum of r1, r2 and r3 is no less than 0 and no greater than 6; and s3 is an integer of 0 to 14.

In the above formula (1-1), p1 is preferably an integer of 0 to 2, more preferably 0 or 1, and still more preferably 0, and p2 is preferably an integer of 0 to 3, more preferably 1 or 2, and still more preferably 2. The sum of p1 and p2 is preferably no less than 1 and no greater than 4, more preferably 2 or 3, and still more preferably 2. In the above formula (1-1), s1 is preferably an integer of 0 to 4, more preferably an integer of 0 to 2, and still more preferably 2.

In the above formula (1-2), q1 is preferably an integer of 0 to 2, more preferably 0 or 1, and still more preferably 0, q2 is preferably an integer of 0 to 2, more preferably 0 or 1, and still more preferably 0, and q3 is preferably an integer of 0 to 2, more preferably 0 or 1, and still more preferably 0. The sum of q1, q2 and q3 is preferably no less than 0 and no greater than 2, more preferably 0 or 1, and still more preferably 0. In the above formula (1-2), s2 is preferably an integer of 0 to 4, more preferably an integer of 0 to 2, and still more preferably 1.

In the above formula (1-3), r1 is preferably an integer of 0 to 2, more preferably 0 or 1, and still more preferably 0, r2 is preferably an integer of 0 to 2, more preferably 0 or 1, and still more preferably 0, and r3 is preferably an integer of 0 to 3, more preferably 1 or 2, and still more preferably 2. The sum of r1, r2 and r3 is preferably no less than 0 and no greater than 4, more preferably 1 or 2, and still more preferably 2. In the above formula (1-3), s3 is preferably an integer of 0 to 4, more preferably an integer of 0 to 2, and still more preferably 2.

The monovalent or the divalent group which may be represented by $R^4$ is exemplified by the group similar to the monovalent or divalent group illustrated as the substituent which the ring structure represented by $X^1$ and $X^2$ may have, and the like.

Examples of the monovalent organic group which may be represented by $R^1$ and $R^2$ in the above formula (1) include monovalent hydrocarbon groups, oxyhydrocarbon groups, acyl groups, acyloxy groups, carbonyloxy hydrocarbon groups, and the like. Of these, each group is exemplified by a group similar to the monovalent group that the ring structure represented by $X^1$ and $X^2$ may have, and the like.

In the above formula (1), a1 and a2 are preferably an integer of 0 to 2, more preferably 0 or 1, and still more preferably 0.

In the above formula (1), n1 and n2 are preferably 0 or 1, and more preferably 0.

In the above formula (1), each of k1 and k2 is preferably an integer of 1 to 4, more preferably an integer of 1 to 3, and still more preferably 1 or 2.

The sum of k1 and k2 is preferably an integer of 3 to 16, more preferably an integer of 3 to 8, still more preferably an integer of 3 to 6, and particularly preferably 3 or 4.

The partial structure (I) is exemplified by structures represented by the following formulae (1-1-1) to (1-3-3) (hereinafter, may be also referred to as "partial structures (I-1-1) to (I-3-3)"), and the like.

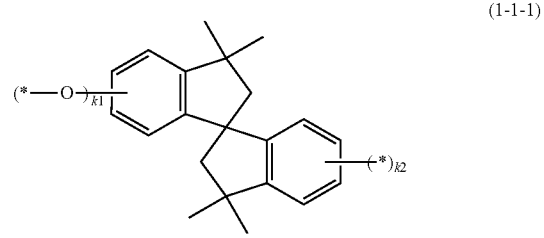

(1-1-1)

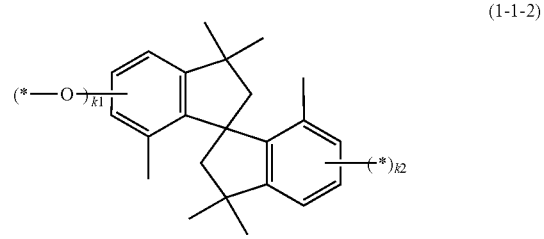

(1-1-2)

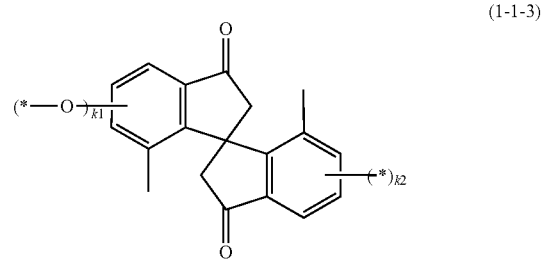

(1-1-3)

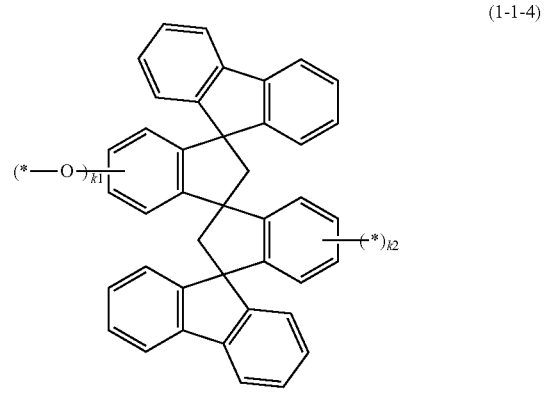

(1-1-4)

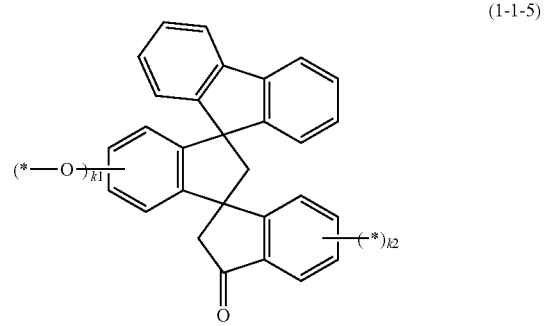

(1-1-5)

-continued (1-1-6)
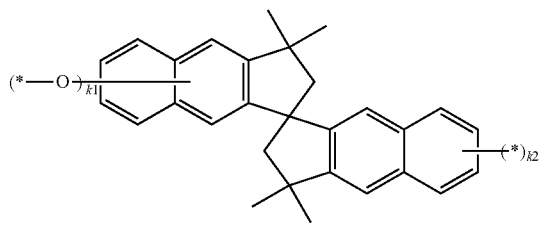

(1-1-7)
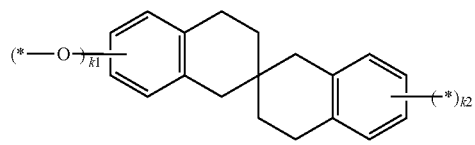

(1-1-8)
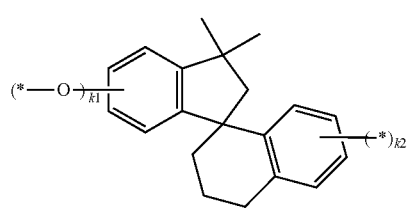

(1-1-9)
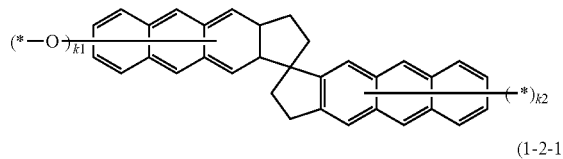

(1-2-1)
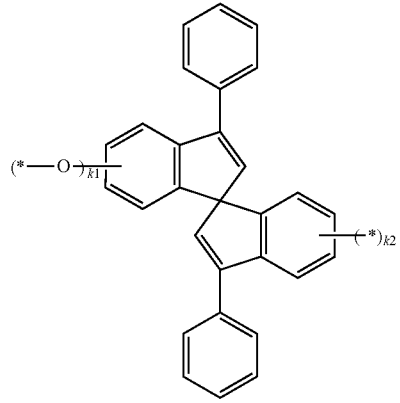

(1-2-2)
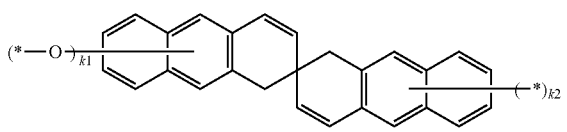

(1-2-3)
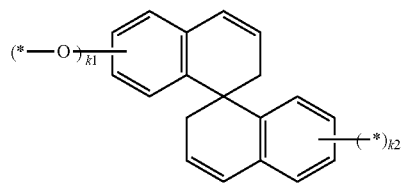

-continued (1-3-1)
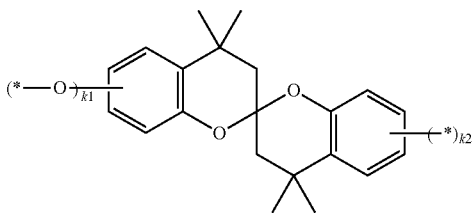

(1-3-2)
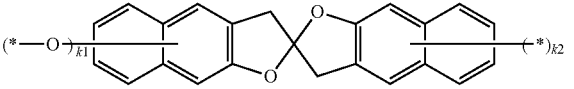

(1-3-3)
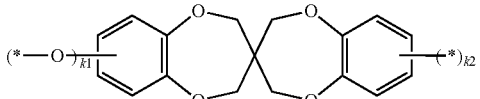

In the above formulae (1-1-1) to (1-3-3), k1 and k2 are each as defined in the above formula (1); and * represents an atomic bonding.

Of these, the partial structure (I) is preferably the partial structures (I-1-1) to (I-1-5), the partial structure (I-2-1) and the partial structure (I-3-1), and more preferably the partial structure (I-1-1).

Modes of the compound (A) are exemplified by compounds having one partial structure (I) (hereinafter, may be also referred to as "(A1) compound" or "compound (A1)"), polymers having at least two partial structures (I) in which the partial structure (I) serves as a repeating unit (hereinafter, may be also referred to as "(A2) polymer" or "polymer (A2)"), and the like. The compound (A1), and the polymer (A2) are explained below in this order.

(A1) Compound

The compound (A1) is a compound having one partial structure (I). When the composition contains the compound (A1) as the compound (A), embedding properties toward the trench can be further improved, and more superior flatness may be attained.

Although the compound (A1) is not particularly limited as long as it has the structure described above, for example, a compound represented by the following formula (2), and the like may be exemplified.

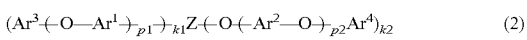

In the above formula (2), Z is the partial structure represented by the above formula (1); k1 and k2 are each as defined in the above formula (1); $Ar^1$ and $Ar^2$ each independently represent a substituted or unsubstituted arenediyl group having 6 to 15 ring atoms; p1 and p2 are each independently an integer of 1 to 3; and $Ar^3$ and $Ar^4$ each independently represent a substituted or unsubstituted aryl group having 6 to 15 ring atoms, wherein in a case where $Ar^1$ to $Ar^4$, p1 and p2 are each present in a plurality of number, the plurality of $Ar^1$s are each identical or different, the plurality of $Ar^2$s are each identical or different, the plurality of $Ar^3$s are each identical or different, the plurality of $Ar^4$s are each identical or different, the plurality of p1s are each identical or different and the plurality of p2s are each identical or different.

Examples of the arenediyl group having 6 to 15 ring atoms represented by $Ar^1$ and $Ar^2$ include a benzenediyl group, a toluenediyl group, a xylenediyl group, a naphthalenediyl group, an anthracenediyl group, and the like.

Examples of the substituent that the arenediyl group may have include halogen atoms such as a fluorine atom, a chlorine atom, a bromine atom and an iodine atom, a hydroxy group, an amino group, a cyano group, a nitro group, an alkoxy group, an alkoxycarbonyl group, an alkoxycarbonyloxy group, an acyl group, an arylaminocarbonyl group, an arylamino group, and the like.

In the above formula (2), p1 and p2 are preferably 1 or 2, and more preferably 1.

Examples of the aryl group having 6 to 15 ring atoms represented by $Ar^3$ and $Ar^4$ include a phenyl group, a tolyl group, a xylyl group, a biphenyl group, a naphthyl group, a methylnaphthyl group, an anthryl group, and the like.

The substituent that the aryl group may have is exemplified by the group similar to those exemplified as the substituent that the arenediyl group represented by $Ar^1$ and $Ar^2$ may have, and the like.

In the above formula (2), each of k1 and k2 is preferably an integer of 1 to 4, more preferably an integer of 1 to 3, and still more preferably 1 or 2.

The sum of k1 and k2 is preferably an integer of 3 to 16, more preferably an integer of 3 to 8, still more preferably an integer of 3 to 6, particularly preferably an integer of 4 to 6, and further particularly preferably 4 or 6.

The compound (A1) is exemplified by compounds represented by the following formulae (2-1) to (2-10) (hereinafter, may be also referred to as "compounds (2-1) to (2-10)"), and the like.

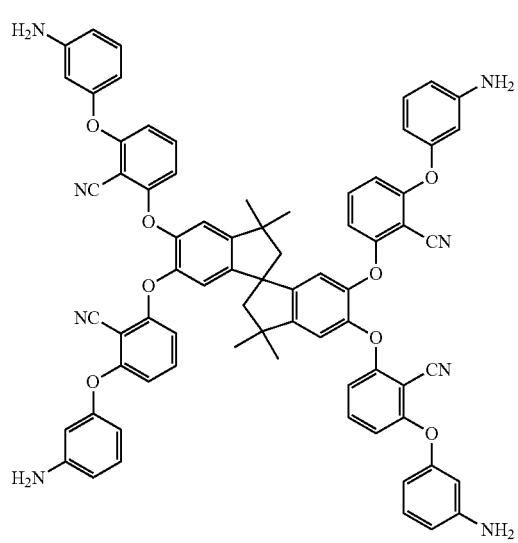

(2-1)

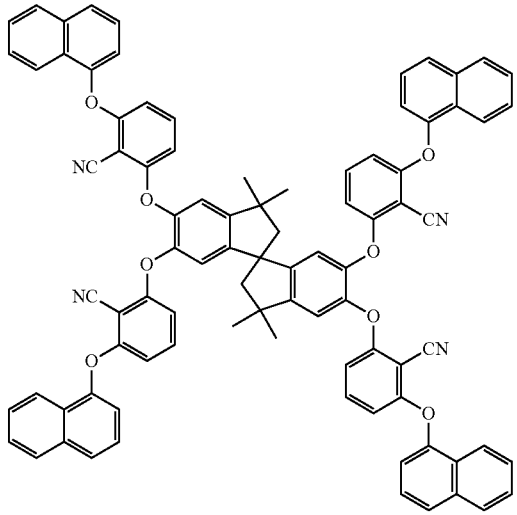

(2-2)

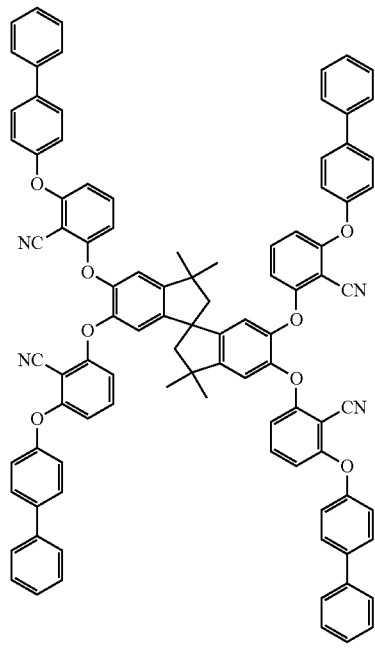

(2-3)

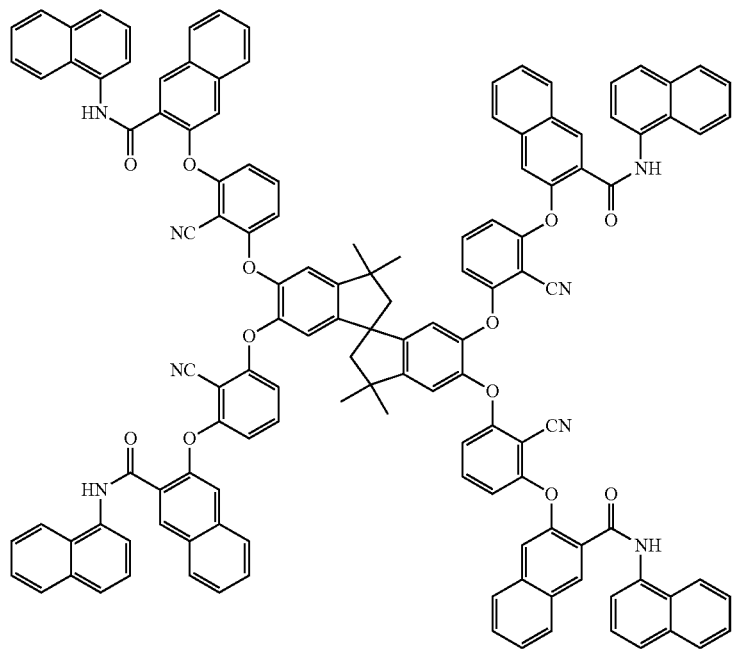
(2-4)
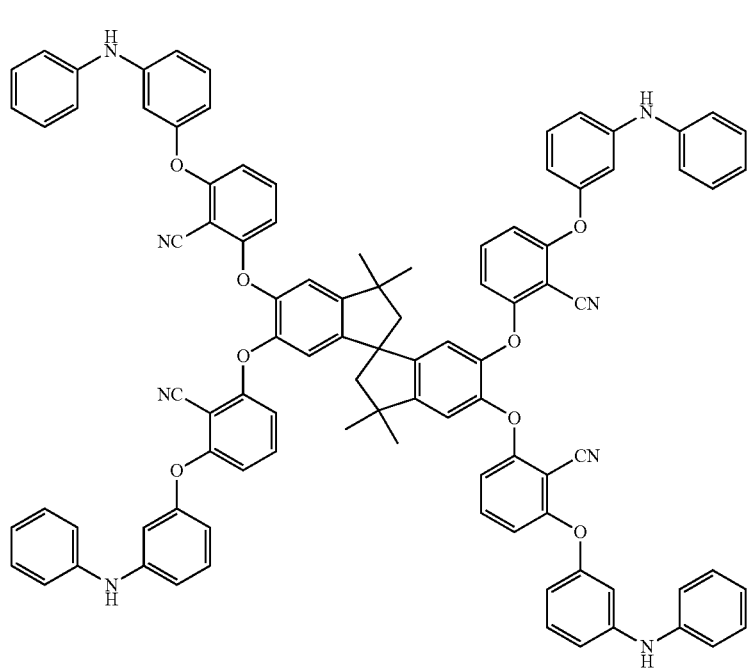
(2-5)

(2-6)
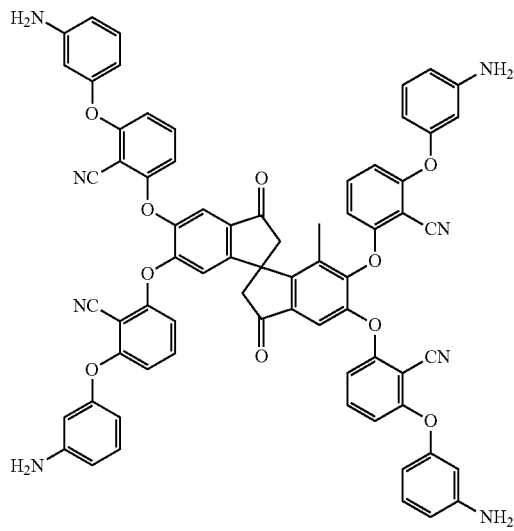
(2-7)
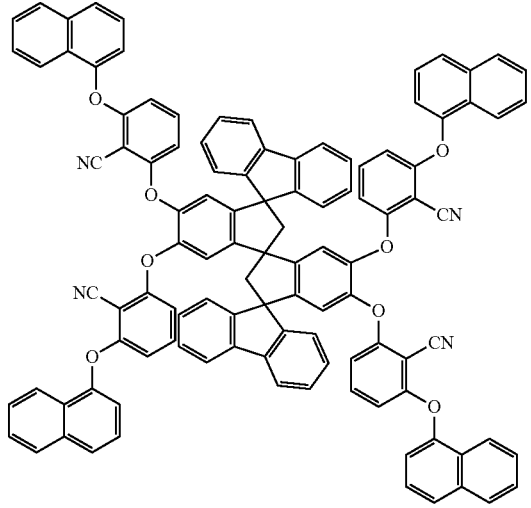
(2-8)
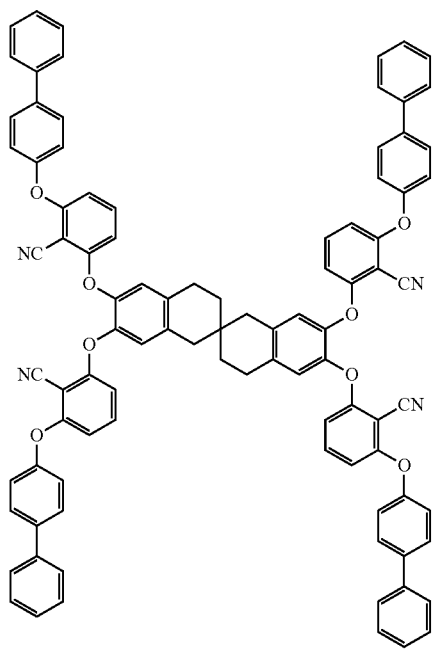

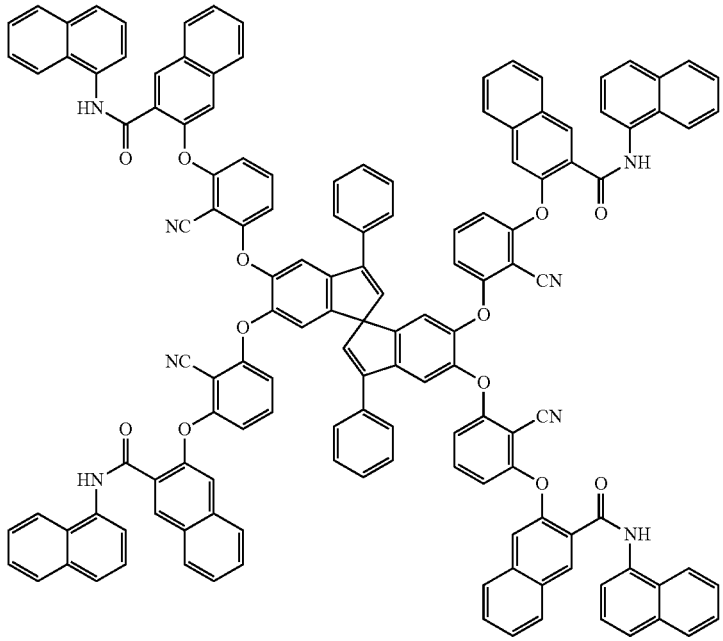

(2-9)

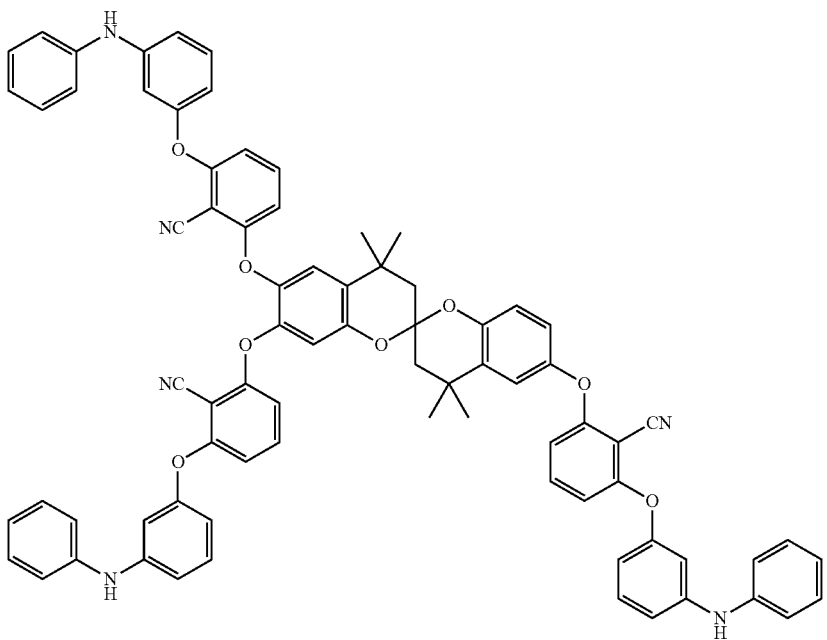

(2-10)

Of these, the compounds (2-1) to (2-5) are preferred.

Synthesis Method of Compound (A1)

The compound (A1) can be synthesized by allowing, for example, a polyol component (A') that includes a polyol compound represented by the following formula (2-m) (hereinafter, may be also referred to as "polyol (2-m)") to react with a monohalo component (B') that includes an aromatic monohalide in an organic solvent, in the presence of an alkali metal or an alkali metal compound. The compound (A1) may be obtained not only by the reaction process described above but also by allowing the polyol component (A') to react with an alkali metal or an alkali metal compound in an organic solvent to obtain an alkali metal salt of the polyol component (A') and thereafter allowing the resulting metal salt to react with the monohalo component (B'). The monohalo component (B') may be obtained by, for example, allowing an aromatic dihalo compound represented by the above formula (2-m) to react with an aromatic mono-ol compound in the presence of a basic compound. Example of the aromatic mono-ol compound include phenol, phenylphenol, aminophenol, naphthol, naphthylaminocarbonylnaphthol, phenylaminophenol, and the like.

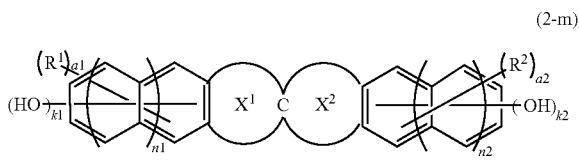

(2-m)

In the above formula (2-m), $X^1$, $X^2$, $R^1$, $R^2$, a1, a2, n1, n2, k1 and k2 are each as defined in the above formula (1).

The basic compound and the organic solvent for use in the reaction is exemplified by compounds similar to those used in the synthesis of the aforementioned polymer (A2), and the like. The amount of the basic compound is, with respect to the —OH group included in the polyol component (A'), preferably 1-fold equivalents to 3-fold equivalents, more preferably 1-fold equivalents to 2-fold equivalents, and still more preferably 1-fold equivalents to 1.5-fold equivalents.

The amount of the monohalo component (B') used is, with respect to the —OH group included in the polyol component (A'), preferably 1-fold equivalents to 3-fold equivalents, more preferably 1-fold equivalents to 2-fold equivalents, and still more preferably 1-fold equivalents to 1.5-fold equivalents.

The reaction temperature is preferably 60° C. to 250° C., and more preferably 80° C. to 200° C. The reaction time is preferably 15 min to 100 hrs, and more preferably 1 hour to 24 hrs.

The compound synthesized may be recovered from the reaction mixture by a reprecipitation technique or the like and then purified. The solvent employed in the reprecipitation is exemplified by alcohol solvents and the like, and of these, methanol is preferred.

The lower limit of the weight average molecular weight (Mw) of the compound (A1) is preferably 600, more preferably 800, and still more preferably 1,000. The upper limit of the Mw of the compound (A1) is preferably 5,000, more preferably 4,000, and still more preferably 3,000.

When the Mw of the compound (A1) falls within the above range, the solubility in PGMEA and the like can be further increased. As a result, the coating properties of the composition can be further improved. In addition, when the Mw falls within the above range, the flatness of the film obtained can be further improved.

(A2) Polymer

The polymer (A2) has the partial structure (I) (hereinafter, may be also referred to as "repeating unit (I)") in a repeating unit. When the composition contains the polymer (A2) as the compound (A), the heat resistance can be further improved. The "polymer" as referred to has at least two repeating units, and may involve both oligomers and polymers as generally classified. When the composition contains the polymer (A2), a film that is superior in heat resistance, solvent resistance and resistance to curving can be formed while general characteristics such as etching resistance are maintained, and superior coating properties, flatness and embedding properties can be achieved. Although the reason for achieving the aforementioned effects when the composition has the aforementioned constitution is not necessarily clear, for example, the reason may be inferred as follows. The polymer (A2) has the repeating unit (I), and this repeating unit (I) has a specific structure as represented by the above formula (1) in which the ring structures $X^1$ and $X^2$ sharing a Spiro carbon atom are each fused with the aromatic ring. The film formed from the composition is believed to achieve the superior heat resistance resulting from this specific structure, and the solvent resistance and the resistance to curving are also improved. In addition, due to having this specific structure, the solubility of the polymer (A) in PGMEA and the like can be increased, whereby use of such a solvent as the solvent (B) of the composition is enabled, and consequently, the coating properties of the composition are improved. Still further, the polymer (A) has a linear polyether structure that includes the repeating unit (I). As a result, it is believed that the composition can exhibit superior flatness and embedding properties.

The polymer (A2) may have a repeating unit (II) and/or a repeating unit (III) as described later in addition to the repeating unit (I), and may further have other repeating unit in addition to these repeating units. Each repeating unit will be explained below.

Repeating Unit (I)

The repeating unit (I) is represented by the above formula (I). Examples of the repeating unit (I) include repeating units represented by the following formulae (1P-1-1) to (1P-3-3) (hereinafter, may be also referred to as "repeating units (1P-1-1) to (1P-3-3)"), and the like.

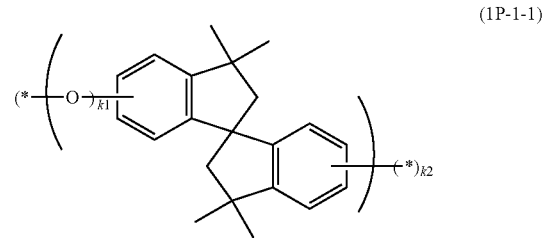

(1P-1-1)

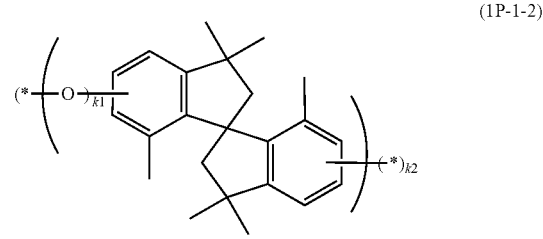

(1P-1-2)

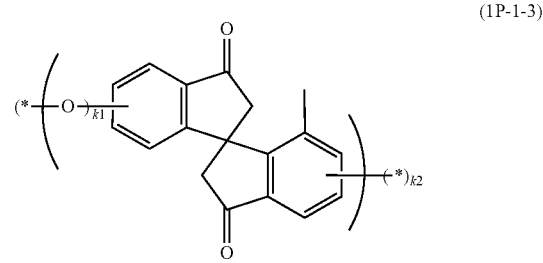

(1P-1-3)

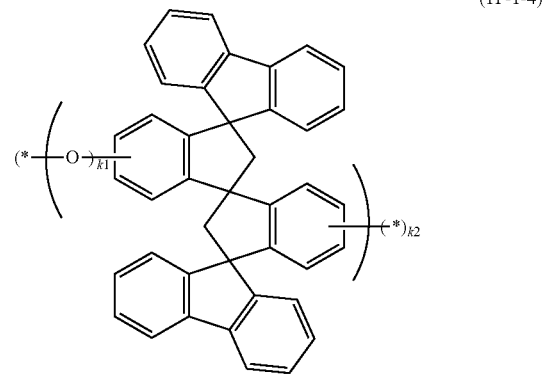

(1P-1-4)

-continued (1P-1-5)
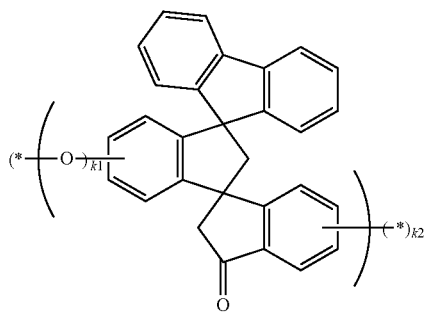

(1P-1-6)
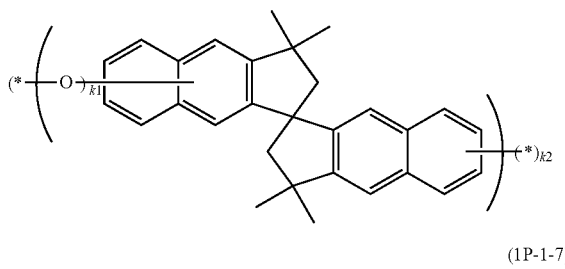

(1P-1-7)
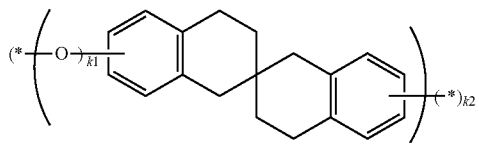

(1P-1-8)
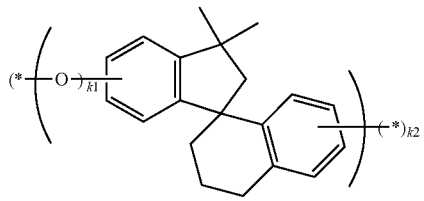

(1P-1-9)
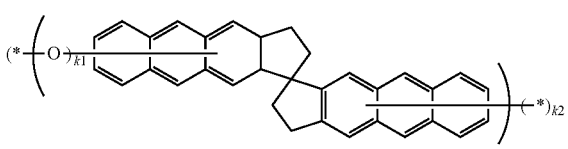

(1P-2-1)
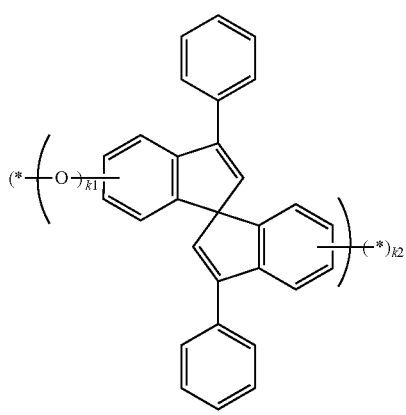

-continued (1P-2-2)
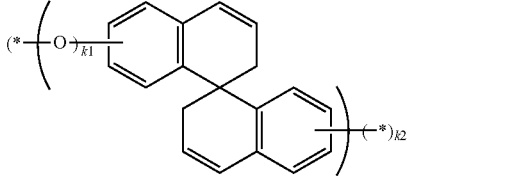

(1P-2-3)
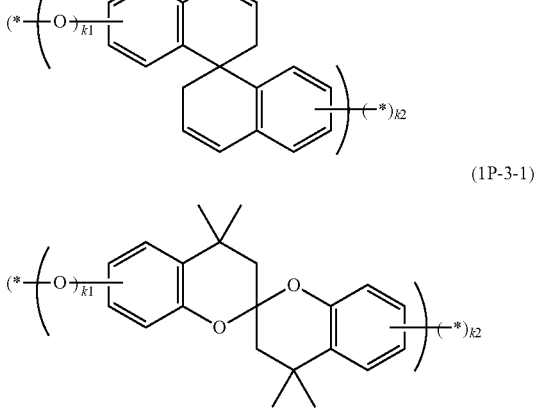

(1P-3-1)
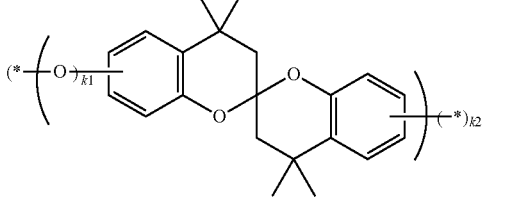

(1P-3-2)

(1P-3-3)
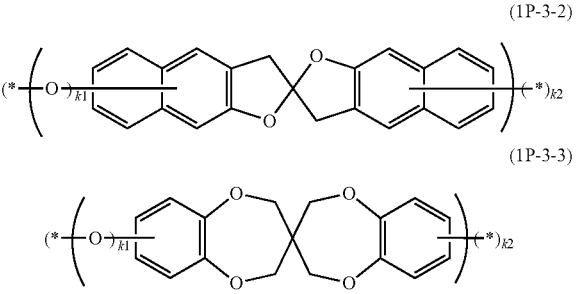

In the above formulae (1P-1-1) to (1P-3-3), k1 and k2 are each as defined in the above formula (1); and * represents an atomic bonding.

Of these, the repeating unit (1P-1-1) and the repeating unit (1P-3-1) are preferred. The repeating unit (1P-1-1) in which the sum of k1 and k2 is no less than 3 and no greater than 6 and the repeating unit (1P-3-1) in which the sum of k1 and k2 is no less than 3 and no greater than 6 are more preferred, and the repeating unit (1P-1-1) in which the sum of k1 and k2 is 4 or 6 and the repeating unit (1P-3-1) in which the sum of k1 and k2 is 4 are still more preferred.

The proportion of the repeating unit (I) contained with respect to the total repeating units constructing the polymer (A2) is, in a case where the sum of k1 and k2 is no less than 3, preferably 0.1 mol % to 20 mol %, more preferably 0.2 mol % to 10 mol %, still more preferably 0.5 mol % to 7 mol %, and particularly preferably 1 mol % to 5 mol %. Whereas, in a case where the sum of k1 and k2 is 1, the proportion of the repeating unit (I) with respect to the total repeating units constructing the polymer (A2) is preferably 5 mol % to 95 mol %, more preferably 10 mol % to 55 mol %, and still more preferably 15 mol % to 35 mol %. When the proportion of the repeating unit (I) contained falls within the above range, various characteristics of the composition can be improved.

Although the polymer (A) may have the repeating unit (I) in any of the main chain and the side chain thereof, the repeating unit (I) is preferably included in the main chain. When the polymer (A) has the repeating unit (I) in the main chain, the composition enables the film formed therefrom to have further superior heat resistance, solvent resistance and resistance to curving, and further improved coating properties, flatness and embedding properties can be provided. The term "main chain" as referred to herein means the longest chain among chains formed through binding of a plurality of atoms constructing the polymer (A). The term "side chain" as referred to herein means any chain other than the main chain among the chains in the polymer (A).

In a case where each of k1 and k2 is 1, the repeating unit including the partial structure represented by the formula (I) is preferably represented by the following formula (X).

In the above formula (X), Z is the partial structure represented by the above formula (1); and $Ar^1$ and $Ar^2$ each independently represent a substituted or unsubstituted arenediyl group having 6 to 40 carbon atoms.

Since the aromatic ring bonds to the oxygen atom bound to the aromatic ring of the structural unit (I) in the polymer (A), in other words, since the polymer (A) is an aromatic polyether having the structural unit (I), the composition provides further improved general characteristics such as etching resistance, as well as further improved heat resistance, solvent resistance, resistance to curving, coating properties, flatness and embedding properties.

Examples of the arenediyl group having 6 to 40 carbon atoms represented by $Ar^1$ and $Ar^2$ include a benzenediyl group, a naphthalenediyl group, an anthracenediyl group, a phenanthrenediyl group, and the like.

Repeating Unit (II)

The repeating unit (II) is represented by the following formula (3). When the polymer (A2) has the repeating unit (II), the solubility in PGMEA and the like can be further increased. As a result, the coating properties of the composition can be improved, and also the optical characteristics and the etching resistance can be improved.

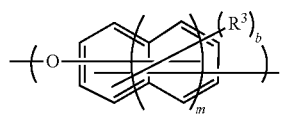

In the above formula (3), $R^3$ represents a halogen atom, a nitro group or a monovalent organic group; b is an integer of 0 to 8, wherein in a case where $R^3$ is present in a plurality of number, the plurality of $R^3$s are identical or different; and m is an integer of 0 to 2.

Example of the halogen atom which may be represented by $R^3$ include a fluorine atom, a chlorine atom, a bromine atom, an iodine atom, and the like. Of these, a fluorine atom and a chlorine atom are preferred, and a chlorine atom is more preferred.

The monovalent organic group which may be represented by $R^3$ is exemplified by groups similar to the monovalent organic groups exemplified for $R^1$ and $R^2$ in the above formula (1), and the like. Of these, a cyano group, and a formyl group are preferred.

$R^3$ represents preferably a halogen atom, a nitro group or a cyano group, more preferably a chlorine atom, a nitro group or a cyano group, and still more preferably a cyano group. When $R^3$ represents an electron-withdrawing group, the polymerization reaction for synthesizing the polymer (A2) can be accelerated.

In the above formula, b is preferably an integer of 0 to 2, more preferably 0 or 1, and still more preferably 0.

In the above formula, m is preferably 0 or 1, and more preferably 0.

In a case where m is 0 in the repeating unit (II), two atomic bondings of the aromatic ring are preferably situated at the meta position. When the atomic bondings in the repeating unit (II) are situated at the meta position, the linearity of the main chain of the polymer (A2) can be reduced, and consequently, the solubility of the polymer (A2) in PGMEA and the like can be further improved.

Examples of the repeating unit (II) include repeating units represented by the following formulae (3-1) to (3-12) (hereinafter, may be also referred to as "repeating units (II-1) to (II-12)"), and the like.

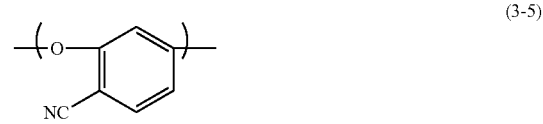

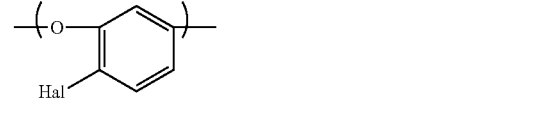

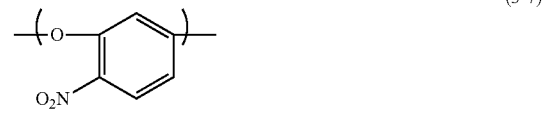

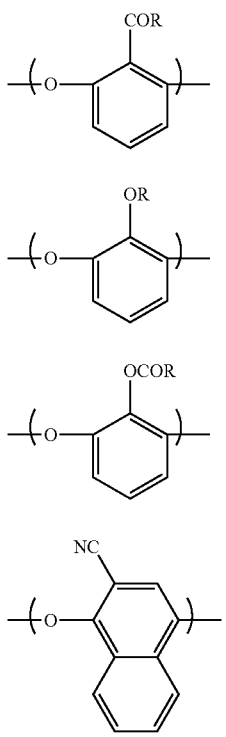

(3-9)

(3-10)

(3-11)

(3-12)

In the above formulae (3-2) and (3-6), Hal represents a halogen atom.

In the above formulae (3-9) to (3-11), R represents a monovalent hydrocarbon group.

Of these, the repeating unit (II) is preferably the repeating units (II-1) to (II-8), (II-12), (II-13), more preferably the repeating units (II-1) to (II-4) and (II-13), and still more preferably the repeating units (II-1) and (II-13).

The proportion of the repeating unit (II) contained with respect to the total repeating units constructing the polymer (A2) is, in a case where the sum of k1 and k2 is no less than 3, preferably 5 mol % to 95 mol %, more preferably 20 mol % to 80 mol %, and still more preferably 30 mol % to 75 mol %. Whereas, in a case where each of k1 and k2 is 1, the proportion of the repeating unit (II) contained with respect to the total repeating units constructing the polymer (A2) is preferably 5 mol % to 95 mol %, more preferably 20 mol % to 80 mol %, and still more preferably 35 mol % to 65 mol %. When the proportion of the repeating unit (II) contained falls within the above range, the solubility of the polymer (A2) in PGMEA and the like can be further increased, and as a result, the coating properties of the composition can be further improved.

Repeating Unit (III)

The repeating unit (III) is represented by the following formula (4). When the polymer (A2) has the repeating unit (III), the heat resistance and the solubility in PGMEA and the like can be further increased. As a result, the coating properties of the composition, and the heat resistance of the film obtained can be further improved.

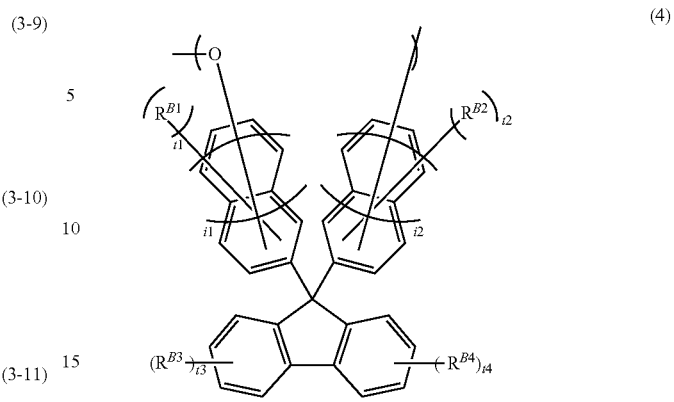

(4)

In the above formula (4), $R^{B1}$ to $R^{B4}$ each independently represent a halogen atom, a nitro group or a monovalent organic group; t1 and t2 are each independently an integer of 0 to 6; t3 and t4 are each independently an integer of 0 to 4; and i1 and i2 are an integer of 0 to 2.

Examples of the halogen atom which may be represented by $R^{B1}$ to $R^{B4}$ include a fluorine atom, a chlorine atom, a bromine atom, an iodine atom, and the like.

The monovalent organic group which may be represented by $R^{B1}$ to $R^{B4}$ is exemplified by groups similar to the monovalent organic groups exemplified for $R^1$ and $R^2$ in the above formula (1), and the like.

$R^{B1}$ to $R^{B4}$ preferably represent a monovalent hydrocarbon group, a halogen atom or a cyano group, and more preferably a monovalent hydrocarbon group.

In the above formula, t1 and t2 are preferably an integer of 0 to 2, more preferably 0 or 1, and still more preferably 0.

In the above formula, t3 and t4 are preferably an integer of 0 to 2, more preferably 0 or 1, and still more preferably 0.

In the above formula, i1 and i2 are preferably 0 or 1, and more preferably 1. It is preferred that i1 and i2 are 1, in other words, a naphthalene ring is provided, since the extinction coefficient of the film formed from the composition can be increased.

Examples of the repeating unit (III) include repeating units represented by the following formulae (4-1) to (4-6) (hereinafter, may be also referred to as "repeating units (III-1) to (III-6)"), and the like.

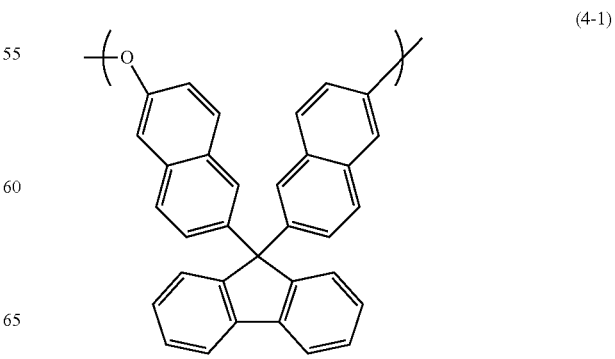

(4-1)

-continued

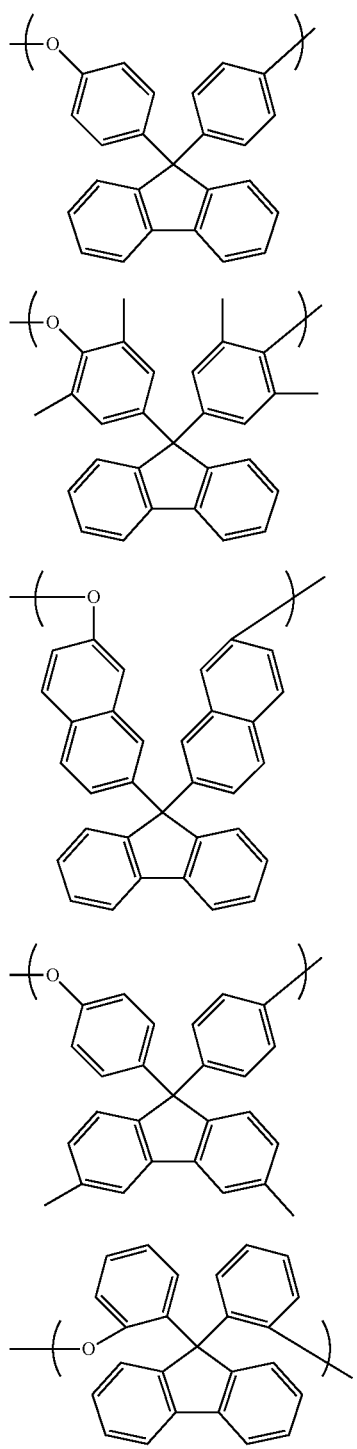

(4-2)

(4-3)

(4-4)

(4-5)

(4-6)

Of these, the repeating unit (III) is preferably the repeating unit (III-1) or the repeating unit (III-2).

The proportion of the repeating unit (III) contained with respect to the total repeating units constructing the polymer (A2) is, in a case where the sum of k1 and k2 is no less than 3, preferably 5 mol % to 95 mol %, more preferably 10 mol % to 70 mol %, and still more preferably 15 mol % to 50 mol %. Alternatively, in a case where each of k1 and k2 is 1, the proportion of the repeating unit (III) contained with respect to the total repeating units constructing the polymer (A2) is preferably 5 mol % to 95 mol %, more preferably 10 mol % to 55 mol %, and still more preferably 15 mol % to 35 mol %. When the proportion of the repeating unit (III) contained falls within the above range, the heat resistance and the solubility in PGMEA and the like of the polymer (A2) can be further increased, and as a result, the coating properties of the composition and the heat resistance of the film obtained can be further improved.

Other Repeating Unit

The polymer (A2) may also have other repeating unit except for the repeating units (I) to (III) described above. Examples of the other repeating unit include repeating units represented by the following formulae (4-1) to (4-6) (hereinafter, may be also referred to as "repeating units (IV-1) to (IV-6)"), and the like.

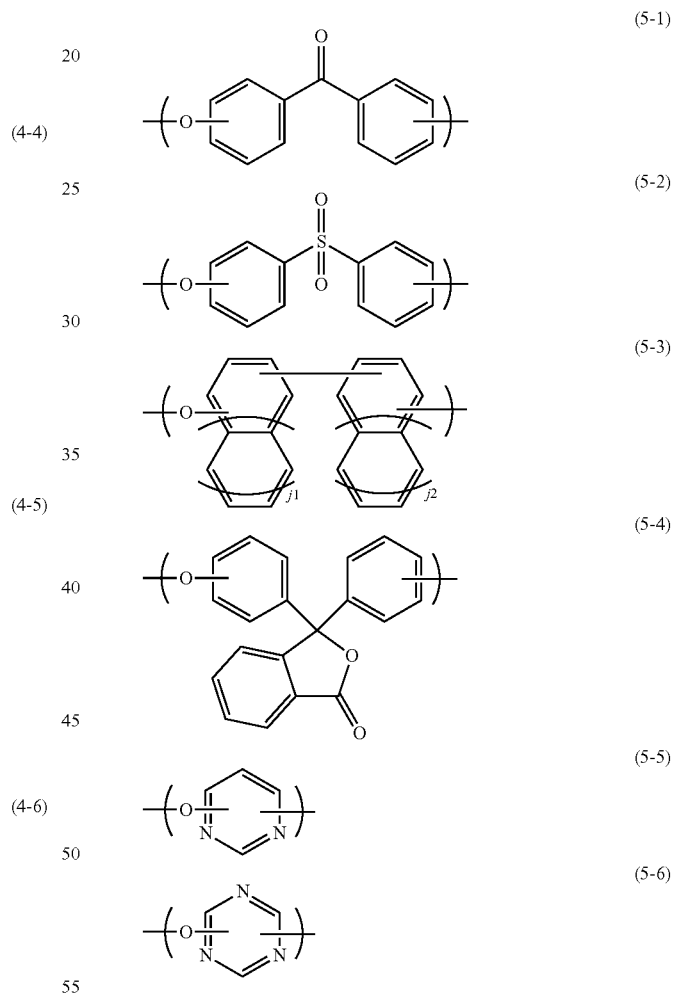

(5-1)

(5-2)

(5-3)

(5-4)

(5-5)

(5-6)

In the above formula (5-3), j1 and j2 are each independently an integer of 0 to 2.

Of these, the other repeating unit is preferably the repeating units (IV-1) to (IV-4).

The polymer (A2) may also have a repeating unit except for the repeating units (IV-1) to (IV-6) aforementioned as the other repeating unit.

This repeating unit may be either one free from an aromatic ring, or one free from an ether group.

The proportion of the other repeating unit contained with respect to the total repeating units constructing the polymer (A2) is, in a case where the sum of k1 and k2 is no less than 3, preferably no greater than 60 mol %, more preferably no greater than 40 mol %, and still more preferably no greater than 10 mol %. Whereas, in a case where each of k1 and k2 is 1, the proportion of the other repeating unit contained with respect to the total repeating units constructing the polymer (A2) is preferably no greater than 30 mol %, more preferably no greater than 20 mol %, and still more preferably no greater than 10 mol %.

The amount of the polymer (A2) contained with respect to the total solid content of the composition is preferably no less than 70% by mass, more preferably no less than 80% by mass, and still more preferably no less than 85% by mass.

Synthesis Method of Polymer (A2)

The polymer (A2) can be synthesized by allowing, for example, the polyol component (A) that includes a polyol compound represented by the following formula (1-m) (hereinafter, may be also referred to as "polyol (1-m)") to react with a dihalo component (B) that includes an aromatic dihalide in an organic solvent, in the presence of an alkali metal or alkali metal compound. The polymer (A2) may be obtained not only by the reaction process described above but also by allowing the polyol component (A) to react with an alkali metal or an alkali metal compound in an organic solvent to obtain an alkali metal salt of the polyol component (A) and thereafter allowing the resulting metal salt to react with the dihalo component (B). The polyol component (A) may also include as needed, for example, a diol compound represented by the following formula (3-m), other diol compound, etc., in addition to the polyol (1-m). The dihalo component (B) is exemplified by a compound represented by the following formula (4-m), and the like.

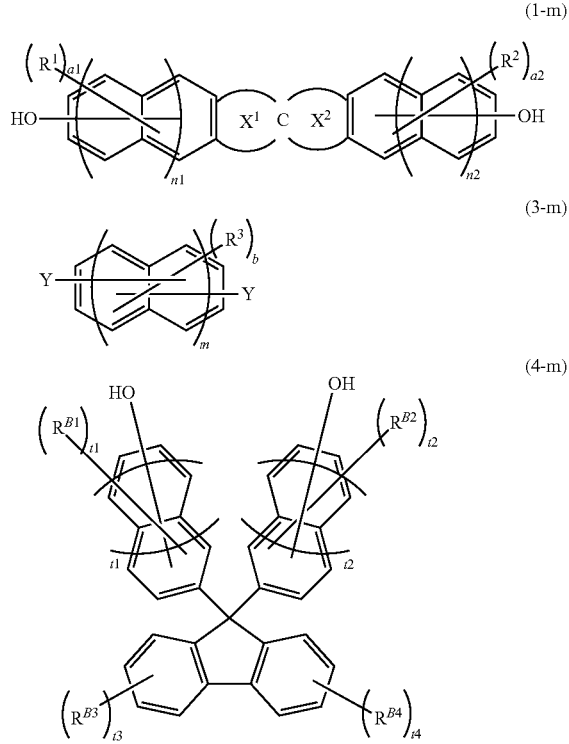

In the above formula (1-m), $X^1$, $X^2$, $R^1$, $R^2$, a1, a2, n1, n2, k1 and k2 are each as defined in the above formula (1).

In the above formula (3-m), $R^3$ and b are each as defined in the above formula (3); and Y represents a halogen atom.

In the above formula (4-m), $R^{B1}$ to $R^{B4}$, t1 to t4, and i1 and i2 are each as defined in the above formula (4).

Examples of the halogen atom represented by Y include a fluorine atom, a chlorine atom, a bromine atom, an iodine atom, and the like. Of these, a fluorine atom and a chlorine atom are preferred, and a fluorine atom is more preferred.

Examples of the alkali metal include lithium, sodium, potassium, and the like.

Examples of the alkali metal compound include:
alkali metal carbonates such as lithium carbonate, sodium carbonate and potassium carbonate;
alkali metal hydrogencarbonates such as lithium hydrogencarbonate, sodium hydrogencarbonate and potassium hydrogencarbonate;
alkali metal hydroxides such as lithium hydroxide, sodium hydroxide and potassium hydroxide;
alkali metal hydrides such as lithium hydride, sodium hydride and potassium hydride; and the like.

Of these, alkali metal carbonates are preferred, and potassium carbonate is more preferred. These alkali metal and alkali metal compounds may be used either alone of one type, or in combination of two or more types thereof.

It is preferred that an electron-withdrawing group is bound to the aromatic ring of the aromatic dihalide in the dihalo component (B) (for example, $R^3$ in the above formula (3-m) being an electron-withdrawing group) since the reaction of the component (A) with the component (B) can be accelerated. Examples of the electron-withdrawing group include a cyano group, a nitro group, and the like.

The amount of the alkali metal or alkali metal compound is, with respect to the —OH group included in the diol component (A), preferably 1-fold equivalents to 3-fold equivalents, more preferably 1-fold equivalents to 2-fold equivalents, and still more preferably 1-fold equivalents to 1.5-fold equivalents.

Examples of the organic solvent for use in the reaction include dimethylacetamide, dimethylformamide, N-methyl-2-pyrrolidone, 1,3-dimethyl-2-imidazolidinone, γ-butyrolactone, sulfolane, dimethyl sulfoxide, diethyl sulfoxide, dimethyl sulfone, diethyl sulfone, diisopropyl sulfone, diphenyl sulfone, diphenyl ether, benzophenone, dialkoxybenzenes in which the alkoxy group has 1 to 4 carbon atoms, and trialkoxybenzenes in which the alkoxy group has 1 to 4 carbon atoms, and the like. Among these solvents, polar organic solvents having a high relative permittivity such as N-methyl-2-pyrrolidone, dimethylacetamide, sulfolane, diphenyl sulfone and dimethyl sulfoxide are preferred. The organic solvents may be used either alone, or in combination of two or more types thereof.

In the reaction, a solvent that forms an azeotropic mixture with water such as benzene, toluene, xylene, hexane, cyclohexane, octane, chlorobenzene, dioxane, tetrahydrofuran, anisole and phenetole may be further used. These solvents may be used either alone, or in combination of two or more types thereof.

In a case where the sum of k1 and k2 is no less than 3, the amount of the polyol component (A) used is, with respect to 100 mol % in total of the polyol component (A) and the dihalo component (B), preferably no less than 45 mol % and no greater than 70 mol %, more preferably no less than 48 mol % and no greater than 65 mol %, and still more preferably no less than 53 mol % and less than 65 mol %. The amount of the dihalo component (B) used is preferably no less than 30 mol % and no greater than 55 mol %, more preferably no less than 35 mol % and no greater than 52 mol %, and still more preferably greater than 35 mol % and no greater than 47 mol %. Furthermore, in a case where each of k1 and k2 is 1, the amount of the polyol (A) used is, with respect to 100 mol % in total of the polyol component (A) and the dihalo component (B), preferably no less than 45 mol % and no greater than 75 mol %, more preferably no less than 48 mol % and no greater than 70 mol %, and still more preferably no less than 60 mol % and less than 70 mol %. The amount of the dihalo component (B) used is preferably no less than 25 mol % and no greater than 55 mol %, more preferably no less than 30 mol % and no greater than 52 mol %, and still more preferably greater than 30 mol % and no greater than 40 mol %.

The reaction temperature falls within a range of preferably 60° C. to 250° C., and more preferably 80° C. to 200° C. The reaction time falls within a range of preferably 15 min to 100 hours, and more preferably 1 hour to 24 hours.

The polymer synthesized may be recovered from the reaction mixture by a reprecipitation technique or the like and then purified. The solvent employed in the reprecipitation is exemplified by alcohol solvents and the like, and of these, methanol is preferred.

In a case where the sum of k1 and k2 is no less than 3, the lower limit of the weight average molecular weight (Mw) of the polymer (A2) is preferably 600, more preferably 1,500, still more preferably 2,500, and particularly preferably 3,000. The upper limit of the Mw of the polymer (A2) is preferably 100,000, more preferably 50,000, still more preferably 15,000, and particularly preferably 6,000. Whereas, in a case where each of k1 and k2 is 1, the lower limit of the Mw of the polymer (A2) is preferably 1,000, more preferably 2,000, and still more preferably 3,000. The upper limit of the Mw of the polymer (A2) is preferably 150,000, more preferably 80,000, and still more preferably 50,000. When the Mw of the polymer (A2) falls within the above range, the solubility in PGMEA and the like can be further increased. As a result, the coating properties of the composition can be further improved. Furthermore, when the Mw falls within the above range, the flatness of the composition, and the heat resistance of the film obtained can be further improved.

The ratio (Mw/Mn) of the weight average molecular weight to the number average molecular weight of the polymer (A2) is preferably no less than 1 and no greater than 5, more preferably no less than 1 and no greater than 3, and still more preferably no less than 1 and no greater than 2.5. When the Mw/Mw ratio of the polymer (A2) falls within the above range, the solubility in PGMEA and the like can be further increased. As a result, the coating properties of the composition can be improved.

The polymer (A2) is preferably obtained by using at least two types of polyol compounds as the polyol component (A). The polymer (A2) obtained in this manner has decreased linearity of the main chain, and consequently, the solubility in PGMEA and the like can be further increased. The at least two types of the polyol compounds are preferably a combination of a compound that gives the repeating unit (I), and a compound that gives a repeating unit other than the repeating unit (I). When such a combination is employed, the linearity of the main chain of the polymer (A2) can be further decreased. In a case where two types of the polyol compounds are used, a combination of a compound that gives the repeating unit (I), and a compound that gives the repeating unit (III) is preferred.

Moreover, in such a polymer (A2), it is preferred that repeating units derived from at least two types of polyol compounds are arranged at random. In other words, it is preferred that the polymerization reaction for synthesizing the polymer (A2) is random copolymerization. When two types of the repeating units are randomly arranged in the polymer (A2), the linearity of the main chain is further decreased, and consequently, the solubility in PGMEA and the like can be further increased.

(B) Solvent

The composition contains the solvent (B). The solvent (B) is not particularly limited as long as the solvent (B) can dissolve or disperse therein the compound (A) and the optional component contained as needed.

Examples of the solvent (B) include alcohol solvents, ketone solvents, amide solvents, ether solvents, ester solvents, and the like. The solvent (B) may be used either alone of one type, or in combination of two or more types thereof.

Examples of the alcohol solvent include:

monohydric alcohol solvents such as methanol, ethanol, n-propanol, iso-propanol, n-butanol, iso-butanol, sec-butanol, t-butanol, n-pentanol, iso-pentanol, sec-pentanol and t-pentanol;

polyhydric alcohol solvents such as ethylene glycol, 1,2-propylene glycol, 1,3-butylene glycol, 2,4-pentanediol, 2-methyl-2,4-pentanediol, 2,5-hexanediol and 2,4-heptanediol; and the like.

Examples of the ketone solvent include:

aliphatic ketone solvents such as acetone, methyl ethyl ketone, methyl n-propyl ketone, methyl n-butyl ketone, diethyl ketone, methyl iso-butyl ketone, methyl n-pentyl ketone, ethyl n-butyl ketone, methyl n-hexyl ketone, di-iso-butyl ketone and trimethylnonanone;

cyclic ketone solvents such as cyclopentanone, cyclohexanone, cycloheptanone, cyclooctanone and methylcyclohexanone;

2,4-pentanedione; acetonyl acetone; diacetone alcohol; acetophenone; methyl n-amyl ketone; and the like.

Examples of the amide solvent include:

cyclic amide solvents such as 1,3-dimethyl-2-imidazolidinone and N-methyl-2-pyrrolidone;

chain amide solvents such as formamide, N-methylformamide, N,N-dimethylformamide, N,N-diethylformamide, acetamide, N-methylacetamide, N,N-dimethylacetamide and N-methylpropionamide; and the like.

Examples of the ether solvent include:

polyhydric alcohol partial ether solvents such as ethylene glycol monomethyl ether, ethylene glycol monoethyl ether and ethylene glycol dimethyl ether;

polyhydric alcohol partial ether acetate solvents such as ethylene glycol monomethyl ether acetate, ethylene glycol monoethyl ether acetate, propylene glycol monomethyl ether acetate (PGMEA) and propylene glycol monoethyl ether acetate;

dialiphatic ether solvents such as diethyl ether, dipropyl ether, dibutyl ether, butyl methyl ether, butyl ethyl ether and diisoamyl ether;

aliphatic-aromatic ether solvents such as anisole and phenyl ethyl ether;

cyclic ether solvents such as tetrahydrofuran, tetrahydropyran and dioxane; and the like.

Examples of the ester solvent include, carboxylic acid ester solvents such as methyl lactate, ethyl lactate, methyl acetate, ethyl acetate, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate and ethyl acetoacetate;

lactone solvents such as γ-butyrolactone and γ-valerolactone;

carbonic acid ester solvents such as diethyl carbonate and propylene carbonate; and the like.

Of these, ether solvents, ketone solvents and ester solvents are preferred, and ether solvents are more preferred. As the ether solvent, polyhydric alcohol partial ether acetate solvents and dialiphatic ether solvents are preferred, polyhydric alcohol partial ether acetate solvents are more preferred, propylene glycol monoalkyl ether acetate is still more preferred, and PGMEA is particularly preferred. As the ketone solvent, methyl n-pentyl ketone and a cyclic ketone solvent are preferred, and cyclohexanone and cyclopentanone are more preferred. As the ester solvent, a carboxylic acid ester solvent and a lactone solvent are preferred, a carboxylic acid ester solvent is more preferred, and ethyl lactate is still more preferred.

Of these, the polyhydric alcohol partial ether acetate solvents are preferred, and among them, propylene glycol monoalkyl ether acetate, particularly PGMEA, is preferably included in the solvent (B) since the coating properties of the composition onto a substrate such as a silicon wafer can be improved. Since the compound (A) contained in the composition has a greater solubility in PGMEA and the like, as a result of including the polyhydric alcohol partial ether acetate solvent in the solvent (B), the composition can achieve superior coating properties. The percentage content of the polyhydric alcohol partial ether acetate solvent in the solvent (B) is preferably no less than 20% by mass, and more preferably no less than 40% by mass.

In a case where each of k1 and k2 is 1, when the polymer (A2) has an Mw of, for example, no less than about 2,000, the solvent (B) is preferably a mixed solvent containing a polyhydric alcohol partial ether acetate solvent, and a ketone solvent and/or an ester solvent in light of an increase of the solubility of the polymer (A2) in the solvent (B), and an improvement of the coating properties of the composition and the like. In this instance, the total of the percentage contents of the ketone solvent and the ester solvent in the solvent (B) is preferably no less than 20% by mass, more preferably no less than 40% by mass, and still more preferably no less than 70% by mass.

(C) Acid Generating Agent

The acid generating agent (C) is a component that generates an acid therefrom by an action of heat and/or lights and facilitates crosslinking of the compound (A). When the composition contains the acid generating agent (C), the crosslinking reaction of the compound (A) may be facilitated and the hardness of the formed film can be further enhanced. The acid generating agent (C) may be used either alone of one type, or in combination of two or more types thereof.

The acid generating agent (C) is exemplified by onium salt compounds, N-sulfonyloxyimide compounds, and the like.

Examples of the onium salt compound include sulfonium salts, tetrahydrothiophenium salts, iodonium salts, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, and the like.

Of these, the acid generating agent (C) is preferably an onium salt compound, more preferably an iodonium salt, and still more preferably bis(4-t-butylphenyl)iodonium nonafluoro-n-butanesulfonate.

The amount of the acid generating agent (C) contained with respect to 100 parts by mass of the compound (A) is preferably 0 parts by mass to 20 parts by mass, more preferably 1 part by mass to 15 parts by mass, and still more preferably 3 parts by mass to 10 parts by mass. When the amount of the acid generating agent (C) contained falls within the above range, the crosslinking reaction of the compound (A) may be more effectively facilitated.

(D) Crosslinking Agent

The crosslinking agent (D) forms a crosslinking bond between molecules of the component such as the compound (A) in the composition by an action of heat and/or an acid. When the composition contains the crosslinking agent (D), the hardness of the formed film can be increased. The crosslinking agent (D) may be used either alone of one type, or in combination of two or more types thereof.

Examples of the crosslinking agent (D) include polyfunctional (meth)acrylate compounds, epoxy compounds, hydroxymethyl group-substituted phenol compounds, alkoxyalkyl group-containing phenol compounds, compounds having an alkoxyalkylated amino group, random copolymers of acenaphthylene with hydroxymethylacenaphthylene represented by the following formula (6-P), compounds represented by the following formulae (6-1) to (6-12), and the like.

Examples of the polyfunctional (meth)acrylate compound include trimethylolpropane tri(meth)acrylate, ditrimethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, glycerin tri(meth)acrylate, tris(2-hydroxyethyl)isocyanurate tri(meth)acrylate, ethylene glycol di(meth)acrylate, 1,3-butanediol di(meth)acrylate, 1,4-butanediol di(meth)acrylate, 1,6-hexanediol di(meth)acrylate, neopentyl glycol di(meth)acrylate, diethylene glycol di(meth)acrylate, triethylene glycol di(meth)acrylate, dipropylene glycol di(meth)acrylate, bis(2-hydroxyethyl)isocyanurate di(meth)acrylate, and the like.

Examples of the epoxy compound include novolac epoxy resins, bisphenol epoxy resins, alicyclic epoxy resins, aliphatic epoxy resins, and the like.

Examples of the hydroxymethyl group-substituted phenol compound include 2-hydroxymethyl-4,6-dimethylphenol, 1,3,5-trihydroxymethylbenzene, 3,5-dihydroxymethyl-4-methoxytoluene (2,6-bis(hydroxymethyl)-p-cresol), and the like.

Examples of the alkoxyalkyl group-containing phenol compound include a methoxymethyl group-containing phenol compound, an ethoxymethyl group-containing phenol compound, and the like.

Examples of the compound having an alkoxyalkylated amino group include nitrogen-containing compounds having a plurality of active methylol groups in a molecule thereof wherein the hydrogen atom of the hydroxyl group of at least one of the methylol groups is substituted with an alkyl group such as a methyl group or a butyl group, and the like; examples thereof include (poly)methylolated melamines, (poly)methylolated glycolurils, (poly)methylolated benzoguanamines, (poly)methylolated ureas, and the like. It is to be noted that a mixture constituted with a plurality of substituted compounds described above may be used as the compound having an alkoxyalkylated amino group, and the compound having an alkoxyalkylated amino group may contain an oligomer component formed through partial self-condensation thereof.

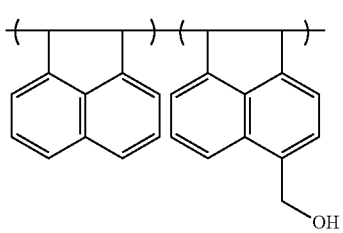

(6-P)

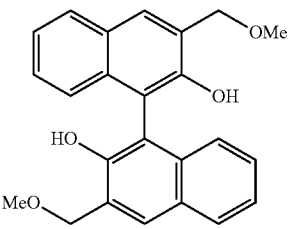

(6-1)

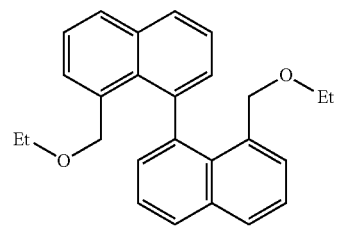

(6-2)

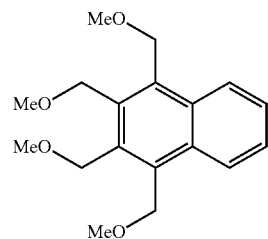

(6-3)

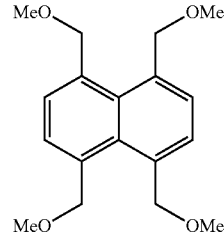

(6-4)

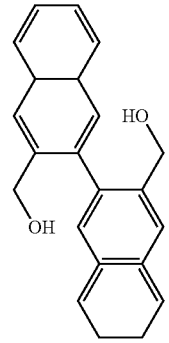

(6-5)

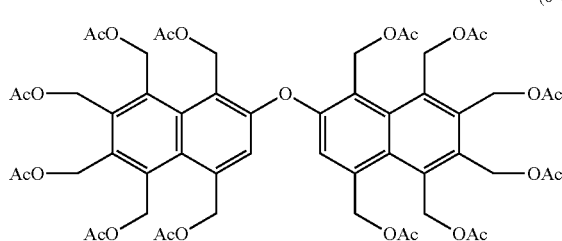

(6-6)

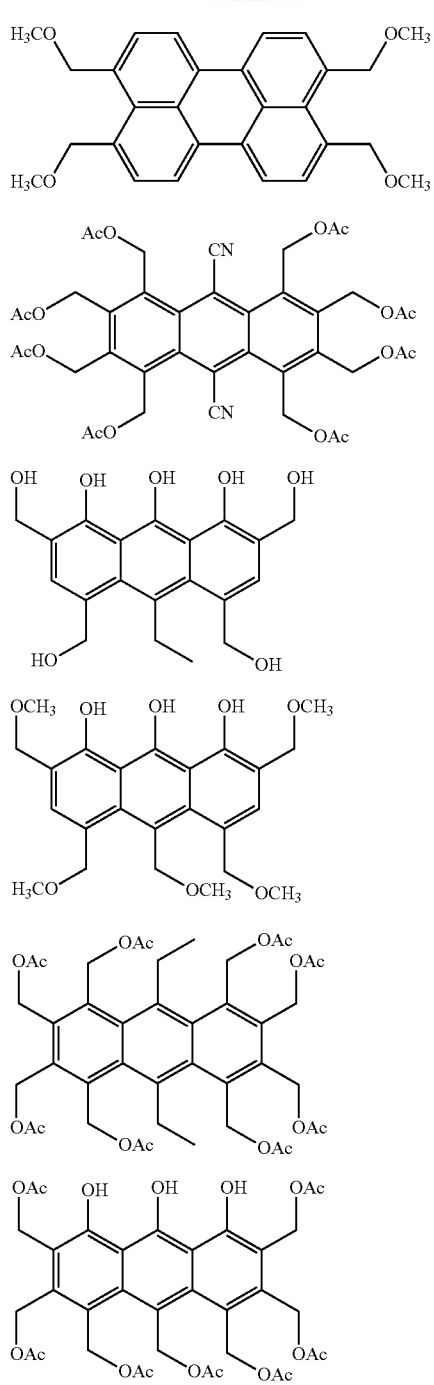

In the above formulae (6-6), (6-8), (6-11) and (6-12), Ac represents an acetyl group.

It is to be noted that the compounds represented by the above formulae (6-1) to (6-12) each may be synthesized with reference to the following documents.

The compound represented by the formula (6-1):
Guo, Qun-Sheng; Lu, Yong-Na; Liu, Bing; Xiao, Jian; and Li, Jin-Shan, Journal of Organometallic Chemistry, 2006, vol. 691, #6, p. 1282-1287.

The compound represented by the formula (6-2):
Badar, Y. et al., Journal of the Chemical Society, 1965, p. 1412-1418.

The compound represented by the formula (6-3):
Hsieh, Jen-Chieh; and Cheng, Chien-Hong, Chemical Communications (Cambridge, United Kingdom), 2008, #2, p. 2992-2994.

The compound represented by the formula (6-4):
Japanese Unexamined Patent Application, Publication No. H5-238990.

The compound represented by the formula (6-5):
Bacon, R. G. R.; and Bankhead, R., Journal of the Chemical Society, 1963, p. 839-845.

The compounds represented by the formulae (6-6), (6-8), (6-11) and (6-12):
Macromolecules, 2010, vol. 43, p. 2832-2839.

The compounds represented by the formulae (6-7), (6-9) and (6-10):
Polymer Journal, 2008, vol. 40, No. 7, p. 645-650; and Journal of Polymer Science: Part A, Polymer Chemistry, Vol. 46, p. 4949-4958.

Among these crosslinking agents (D), a methoxymethyl group-containing phenol compound, a compound having an alkoxyalkylated amino group, and a random copolymer of acenaphthylene with hydroxymethylacenaphthylene are preferred, a compound having an alkoxyalkylated amino group is more preferred, and 1,3,4,6-tetra(methoxymethyl)glycoluril is still more preferred.

The amount of the crosslinking agent (D) contained with respect to 100 parts by mass of the compound (A) is preferably 0 to 100 parts by mass, more preferably 0.5 parts by mass to 50 parts by mass, still more preferably 1 part by mass to 30 parts by mass, and particularly preferably 3 parts by mass to 20 parts by mass. When the amount of the crosslinking agent (D) contained falls within the above range, the crosslinking reaction of the compound (A) may be allowed to cause more effectively.

Other Optional Component

The other optional component is exemplified by a surfactant, an adhesion aid, and the like.

Surfactant

When the composition contains a surfactant, the coating properties can be improved, and as a result, uniformity of the surface of the film provided may be improved, and occurrence of the unevenness of coating can be inhibited. The surfactant may be used either alone of one type, or in combination of two or more types thereof.

Examples of the surfactant include a nonionic surfactant such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, polyethylene glycol distearate, and the like. Also, examples of commercially available products include KP341 (manufactured by Shin-Etsu Chemical Co., Ltd.), Polyflow No. 75 and No. 95 (each manufactured by Kyoeisha Chemical Co., Ltd.), F-top EF101, EF204, EF303 and EF352 (each manufactured by Tochem Products Co. Ltd.), Megaface F171, F172 and F173 (each manufactured by Dainippon Ink And Chemicals, Incorporated), Fluorad FC430, FC431, FC135 and FC93 (each manufactured by Sumitomo 3M Limited), ASAHI GUARD AG710, Surflon S382, SC101, SC102, SC103, SC104, SC105 and SC106 (each manufactured by Asahi Glass Co., Ltd.), and the like.

The amount of the surfactant (E) contained with respect to 100 parts by mass of the compound (A) is preferably 0 parts by mass to 10 parts by mass, more preferably 0.001 parts by mass to 5 parts by mass, and still more preferably 0.005 parts by mass to 1 part by mass. When the amount of the surfactant contained falls within the above range, the coating properties of the composition can be further improved.

Adhesion Aid

The adhesion aid is a component that improves adhesiveness to an underlying material. When the composition contains the adhesion aid, the adhesiveness of the formed film to a substrate, etc., as an underlying material can be improved. The adhesion aid may be used either alone of one type, or in combination of two or more types thereof.

Well-known adhesion aids may be used as the adhesion aid.

The amount of the adhesion aid contained with respect to 100 parts by mass of the compound (A) is preferably 0 parts by mass to 10 parts by mass, more preferably 0.01 parts by mass to 10 parts by mass, and still more preferably 0.01 parts by mass to 5 parts by mass.

Preparation Method of Composition

The composition may be prepared by mixing the compound (A) and the solvent (B), and as needed, the acid generating agent (C), the crosslinking agent (D) and other optional component(s) in a predetermined ratio. The solid content concentration of the composition is preferably 0.1% by mass to 50% by mass, more preferably 1% by mass to 30% by mass, still more preferably 3% by mass to 20% by mass, and particularly preferably 5% by mass to 15% by mass.

While superior coating properties are achieved, as described above, the composition enables a film that is superior in heat resistance and flatness to be formed, and is thus suitable for film formation. Among compositions for use in film formation, the composition can be particularly suitably used for resist underlayer film formation in multilayer resist processes and the like for which these characteristics are demanded at a high level. Furthermore, in a case where each of k1 and k2 is 1, the film is also superior in the solvent resistance and the resistance to curving. In a case where the compound (A) is the polymer (A2), and each of k1 and k2 is 1, the composition can form a film that is superior in both the optical characteristics such as transparency, as well as the thermal characteristics such as heat resistance, and the film can be suitably used also as an optical film, a printed wiring substrate, an insulating film, a protective film, and the like.

Method for Producing Patterned Substrate

The method for producing a patterned substrate according to another embodiment of the present invention includes the steps of:

forming a resist underlayer film on the upper face side of a substrate (hereinafter, may be also referred to as "resist underlayer film formation step");

forming a resist pattern directly or indirectly on the resist underlayer film (hereinafter, may be also referred to as "resist pattern formation step"); and etching at least the resist underlayer film and the substrate using the resist pattern as a mask such that the substrate has a pattern (hereinafter, may be also referred to as "substrate pattern formation step").

The resist underlayer film is formed from the composition.

According to the method for producing a patterned substrate, while superior coating properties are achieved, a resist underlayer film that is superior in the heat resistance, solvent resistance, resistance to curving, flatness and embedding properties can be readily formed. Thus, formation of a favorable pattern is enabled.

Resist Underlayer Film Formation Step

In this step, a resist underlayer film is formed on the upper face side of a substrate from the composition. The formation of the resist underlayer film is typically carried out by applying the composition on the upper face side of the substrate to provide a coating film, and heating the coating film.

Examples of the substrate include a silicon wafer, a wafer coated with aluminum, and the like. Moreover, the method for coating the composition on the substrate is not particularly limited, and for example, an appropriate process such as a spin-coating process, a cast coating process and a roll coating process may be employed.

Heating of the coating film is typically carried out in an ambient air. The heating temperature falls within a range of typically 150° C. to 500° C., and preferably 200° C. to 450° C. When the heating temperature is less than 150° C., the oxidative crosslinking may not sufficiently proceed, and characteristics necessary for use in the resist underlayer film may not be exhibited. The heating time falls within a range of typically 30 sec to 1,200 sec, and preferably 60 sec to 600 sec.

An oxygen concentration in the heating is preferably no less than 5 vol %. When the oxygen concentration in the heating is low, the oxidative crosslinking of the resist underlayer film may not sufficiently proceed, and characteristics necessary for use in the resist underlayer film may not be exhibited.

The coating film may be preheated at a temperature of 60° C. to 250° C. before being heated at a temperature of 150° C. to 500° C. Although the preheating time in the preheating is not particularly limited, the preheating time is preferably 10 sec to 300 sec, and more preferably 30 sec to 180 sec. When the preheating is carried out to preliminarily evaporate a solvent and make the film dense, dehydrogenation reaction may efficiently proceed.

It is to be noted that in the resist underlayer film formation method, the resist underlayer film is typically formed through the heating of the coating film; however, in a case where the composition for forming a resist underlayer film contains a photo acid generating agent, the resist underlayer film may also be formed by curing the coating film through a combination of an exposure and heating. Radioactive ray used for the exposure may be appropriately selected from visible rays, ultraviolet rays, far ultraviolet rays, X-rays, electron beams, γ radiations, molecular beams, ion beams, and the like depending on the type of the photo acid generating agent.

The film thickness of the resist underlayer film formed is preferably 0.05 μm to 5 μm, and more preferably 0.1 μm to 3 μm.

After the resist underlayer film formation step, the method may further include as needed, the step of forming an intermediate layer (intermediate film) on the resist underlayer film. The intermediate layer as referred to means a layer having a function that is exhibited or not exhibited by the resist underlayer film and/or the resist film in resist pattern formation in order to further compensate for the function exhibited by the resist underlayer film and/or the resist film, or to impart to the resist underlayer film and/or the resist film a function not exhibited thereby. For example, when an antireflective film is provided as the intermediate layer, an antireflecting function of the resist underlayer film may be further enhanced.

The intermediate layer may be formed from an organic compound and/or an inorganic oxide. Examples of the organic compound include commercially available products such as "DUV-42", "DUV-44", "ARC-28" and "ARC-29" (each manufactured by Brewer Science); "AR-3" and "AR-19" (each manufactured by Lohm and Haas Company); and the like. Examples of the inorganic oxide include commercially available products such as "NFC SOG01", "NFC SOG04", "NFC SOG080" (each manufactured by JSR), and the like. Moreover, polysiloxanes, titanium oxides, alumina oxides, tungsten oxides, and the like that are provided through a CVD process may be used.

The method for providing the intermediate layer is not particularly limited, and for example, a coating method, a CVD technique, or the like may be employed. Of these, a coating method is preferred. In a case where the coating method is employed, the intermediate layer may be successively provided after the resist underlayer film is provided. Moreover, the film thickness of the intermediate layer is not particularly limited and may be appropriately selected depending on the function required for the intermediate layer, and the film thickness of the intermediate layer falls within a range of preferably 10 nm to 3,000 nm, and more preferably 20 nm to 300 nm.

Resist Pattern Formation Step

In this step, a resist pattern is formed directly or indirectly on the resist underlayer film. This step may be carried out by, for example, using a resist composition.

When the resist composition is used, specifically, the resist film is formed by coating the resist composition such that a resultant resist film has a predetermined film thickness and thereafter subjecting the resist composition to prebaking to evaporate the solvent in the coating film.

Examples of the resist composition include a positive or negative chemically amplified resist composition that contains a photo acid generating agent; a positive type resist composition that is constituted with an alkali-soluble resin and a quinone diazide based photosensitizing agent; a negative type resist that is constituted with an alkali-soluble resin and a crosslinking agent; and the like.

The total solid content concentration in the resist composition typically falls within a range of 1% by mass to 50% by mass. Moreover, the resist composition is generally used for providing a resist film, for example, after being filtered through a filter with a pore size of about 0.2 μm. It is to be noted that a commercially available resist composition may be used as is in this step.

The method for coating the resist composition is not particularly limited, and examples thereof include a spin-coating method, and the like. Moreover, the temperature of the prebaking may be appropriately adjusted depending on the type of the resist composition used and the like, and the temperature of the prebaking falls within a range of generally 30° C. to 200° C., and preferably 50° C. to 150° C.

Next, the resist film formed is exposed by selective irradiation with a radioactive ray. The radioactive ray for use in the exposure may be appropriately selected from visible rays, ultraviolet rays, far ultraviolet rays, X-rays, electron beams, γ radiations, molecular beams, ion beams and the like, depending on the type of the photo acid generating agent used in the resist composition. Among these, far ultraviolet rays are preferred, and a KrF excimer laser beam (248 nm), an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm), extreme-ultraviolet rays (wavelength: 13 nm, etc.) and the like are more preferred.

Post-baking may be carried out after the exposure for the purpose of improving a resolution, a pattern profile, developability, and the like. The temperature of the post-baking may be appropriately adjusted depending on the type of the resist composition used and the like, and the temperature of the post-baking falls within a range of typically 50° C. to 200° C., and preferably 70° C. to 150° C.

Next, the exposed resist film is developed with a developer solution to form a resist pattern. The developer solution may be appropriately selected depending on the type of the resist composition used. In the case of a development with an alkali, examples of the developer solution include an alkaline aqueous solution that contains sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, 1,5-diazabicyclo[4.3.0]-5-nonene, or the like. An appropriate amount of a water soluble organic solvent, e.g., an alcohol such as methanol and ethanol, a surfactant, and the like may be added to the alkaline aqueous solution. Alternatively, in the case of a development with an organic solvent, examples of the developer solution include a variety of organic solvents exemplified as the solvent (B) described above, and the like.

A predetermined resist pattern is formed by the development with the developer solution, followed by washing and drying.

In carrying out the resist pattern formation step, without using the resist composition as described above, other process may be employed, for example, a nanoimprint method may be adopted, or a directed self-assembling composition may be used.

Substrate Pattern Formation Step

In this step, at least the resist underlayer film and the substrate are etched using the resist pattern as a mask such that the substrate has a pattern. In a case where the intermediate layer is not provided, the resist underlayer film and the substrate are subjected to etching sequentially in this order, whereas in a case where the intermediate layer is provided, the intermediate layer, the resist underlayer film and the substrate are subjected to etching sequentially in this order. The etching procedure may be exemplified by dry etching, wet etching, and the like. Of these, dry etching is preferred. For example, gas plasma such as oxygen plasma and the like may be used in the dry etching. After the dry etching, the substrate having a predetermined pattern can be obtained.

Method for Forming Film

The method for forming a film according to yet another embodiment of the present invention includes the steps of:

providing a coating film (hereinafter, may be also referred to as "coating film-providing step"); and removing a solvent from the coating film (hereinafter, may be also referred to as "solvent-removing step"). The coating film is provided by using the composition described above.

In addition, it is preferred that the method for forming a film further includes the step of baking the coating film after removing the solvent (hereinafter, may be also referred to as "baking step").

According to the method for forming a film, since the composition described above is used, a uniform film can be readily formed which is superior in both optical characteristics such as total light transmittance and haze, and thermal characteristics such as heat resistance, and is accompanied by less turbidity and roughness.

Coating Film Providing-Step

In the coating film-providing step, the coating film is provided by using the composition described above.

Examples of the substrate on which the coating film is provided include a polyethylene terephthalate (PET) film, a silicon wafer, a glass wafer, a glass substrate, an SUS plate, and the like. Since the composition is used, formation of a thin film is enabled even in a case where a substrate such as a silicon wafer, a glass wafer, a glass substrate or an SUS plate, having a low affinity to polymers and/or solvents is used.

As the process for coating the composition, for example, a roll coating process, a gravure coating process, a spin-coating process, a doctor blade process, or the like may be employed.

Although the thickness of the coating film is not particularly limited, the thickness is typically 0.1 μm to 250 μm, preferably 2 μm to 150 μm, and more preferably 5 μm to 125 μm.

Solvent-Removing Step

In the solvent-removing step, the solvent is removed from the coating film.

As a procedure of removing the solvent from the coating film, for example, evaporation of the solvent in the coating film may be exemplified. For this purpose, for example, heating of the coating film, subjecting the coating film to a reduced pressure condition, employing the heating and the reduced pressure in combination, and the like may be exemplified. Of these, heating of the coating film is preferably employed.

The heating condition may be appropriately selected in accordance with the substrate and/or the polymer, as long as the solvent is evaporated. For example, the heating temperature is preferably 30° C. to 300° C., more preferably 40° C. to 250° C., and still more preferably 50° C. to 230° C. The heating time period is preferably 10 min to 5 hrs.

The heating may be carried out with two or more steps. Specifically, for example, heating at 30° C. to 80° C. for 10 min to 2 hrs is followed by further heating at 100° C. to 250° C. for 10 min to 2 hrs.

Although the atmosphere in heating is not particularly limited, the heating is conducted preferably in the ambient air, or in an inert gas atmosphere, and more preferably in an inert gas atmosphere. The inert gas is, in light of the inhibition of coloring of the provided film, preferably nitrogen, argon or helium, and more preferably nitrogen.

Alternatively, the solvent-removing step may be carried out on the entirety of the substrate having the coating film provided thereon: however, in light of a decrease of influences from the properties of the substrate, it is preferred that after removing a part of the solvent (for example, after the heating in the first step when the heating is conducted with two steps as described above), the coating film is separated from the substrate, and thereafter, the solvent is removed from the coating film thus separated.

Baking Step

In the baking step, the coating film after removing the solvent is baked.

When the baking step is further included in the method for forming a film, a film that exhibits a small rate of thermal shrinkage can be obtained.

In the baking step, the entirety of the substrate having the coating film provided thereon may be baked; however, in light of a decrease of influences from the properties of the substrate, it is preferred that the coating film provided on the substrate is separated from substrate, and thereafter, the baking is conducted.

It is to be noted that the solvent-removing step may be carried out concomitantly with the baking step, or the solvent-removing step may be carried out before the baking step. When the coating film separated from the substrate is baked, it is preferred that the solvent is removed beforehand from the coating film before separating the coating film from the substrate.

The baking temperature is preferably 210° C. to 350° C., more preferably 220° C. to 330° C., and still more preferably 230° C. to 320° C. The baking time period is preferably 10 min to 5 hrs.

Although the atmosphere in baking is not particularly limited, the heating is conducted preferably in the ambient air, or in an inert gas atmosphere, and more preferably in an inert gas atmosphere. The inert gas is, in light of the inhibition of coloring of the provided film, preferably nitrogen, argon or helium, and more preferably nitrogen.

The film thus obtained may be used after separating from the substrate, or depending on the intended usage and/or the type of the substrate used, the film may be used as is, without separating from the substrate.

The thickness of the film may be appropriately selected in accordance with the intended usage, and is preferably 0.05 μm to 250 μm, more preferably 2 μm to 150 μm, and still more preferably 10 μm to 125 μm.

Compound

The compound according to other embodiment of the present invention has the partial structure (I).

Since the compound has the partial structure (I), it can be suitably used as a component of the composition described above, and this composition is, while general characteristics such as etching resistance are maintained, also superior in heat resistance, as well as coating properties and flatness. Moreover, in a case where each of k1 and k2 is 1, the compound can form a film that is also superior in solvent resistance and resistance to curving, and this compound is superior in both optical characteristics such as transparency, and thermal characteristics such as heat resistance.

The compound corresponds to the compound (A) contained in the composition described above, and the explanation has been presented as in the foregoing.

Film

The film according to still other embodiment of the present invention includes the compound described above. Since the film includes the compound described above, it is superior in both the optical characteristics such as transparency, and the thermal characteristics such as heat resistance. Such a film can be suitably used as an optical waveguide plate, a polarizing plate, a film for displays, an film for optical discs, a transparent electric conductive film, and an optical waveguide plate. Furthermore, the film can be suitably used as a substrate for printed wiring such as substrates for conductor flexible printed wiring of mobile phones, touchscreens, electronic papers and the like, substrates for rigid printed wiring, substrates for photoelectronic printed wiring, and substrates for COF (Chip on Film), TAB (Tape Automated Bonding). In addition, since the film can be formed to be thin, it is particularly suitable as various types of film condensers, insulating films, protective films, resist underlayer films, and the like.

Composite

A composite is also one suitable embodiment in which the compound is used.

The composite includes:

a base material containing the compound, and at least one member which is provided on at least one face of the base material and is selected from the group consisting of a transparent conductive film, a colored part and a switching element.

Since the composite has the base material containing the compound described above, it is superior in both the optical characteristics such as transparency, and the thermal characteristics such as heat resistance.

Specific exemplary composite includes optical components, etc., such as: a transparent electrically conductive film having a transparent conductive film on at least one face of the base material, a color filter substrate having a colored part on at least one face of the base material, and a switching element substrate having a switching element on at least one face of the base material.

Transparent Electric Conductive Film

The transparent electric conductive film described above includes a transparent conductive film on at least one face of the base material.

The transparent conductive film is not particularly limited as long as it is transparent and exhibits electric conductivity, and examples of the transparent conductive film include metal oxide films constituted with tin oxide, indium oxide, antimony oxide, zinc oxide, cadmium oxide, indium tin oxide (ITO), indium zinc oxide (IZO) or the like, as well as composite films predominantly including any of these metal oxides, and a metal film constituted with gold, silver, copper, tin, nickel, aluminum, palladium or the like, and the like.

The process for forming the transparent conductive film is not particularly limited, and is exemplified by well-known processes such as a vacuum deposition process, a sputtering process, an ion plating process and a CVD process. In light of uniformity of the film, and the adhesiveness of a thin film to the base material, thin film formation by a sputtering process is preferred.

The temperature in forming a film constituted with a metal, metal oxide or the like by a sputtering process, etc., is preferably 150 to 350° C., more preferably 180 to 300° C., and still more preferably 220 to 260° C.

Since the base material includes the compound described above, it has a high glass transition temperature. Thus, even if such a process that necessitates heating at such a high temperature should be executed, formation of a transparent conductive film on the base material is enabled, whereby a transparent electric conductive film having superior electric characteristics and high reliability can be produced.

Alternatively, the transparent conductive film may be formed by coating a polythiophene- or polyaniline-based electrically conductive polymer on the base material to permit film formation.

The thickness of the transparent conductive film is preferably no less than 30 Å. When the thickness is less than 30 Å, a continuous coating film may be less likely to be formed which has a favorable electric conductivity to give a specific resistance (volume resistivity) of no greater than $1 \times 10^{-3}$ Ω·cm. On the other hand, when the thickness is too great, a disadvantage such as deterioration of the transparency may be caused. Accordingly, the thickness of the transparent conductive film is suitably about 50 to 2000 Å.

The transparent conductive film may be composed of either a single layer, or a multilayer.

When the transparent conductive film is formed on the base material, in light of an improvement of the adhesiveness between the base material and the transparent conductive film, the surface of the base material is preferably subjected to a surface treatment beforehand, such as a plasma treatment, a corona treatment, an alkali treatment or a coating treatment.

The transparent electric conductive film may have an antireflective film, a hard coating film or the like if desired on at least one face thereof, and may be subjected to an anti-Newton ring treatment.

The transparent electric conductive film has a specific resistance value (volume resistivity value) as determined by using Low Resistivity Meter "Loresta-GP" manufactured by Mitsubishi Chemical Analytech Co., Ltd. of preferably no greater than $2 \times 10^{-3}$ Ω·cm, and more preferably no greater than $5 \times 10^{-4}$ Ω·cm. The specific resistance value falling within the above range is preferred since a film having favorable electric conductivity is provided, and a touchscreen that includes such a film can precisely and quickly respond even to delicate maneuvers.

The composite preferably has a polarizing plate on at least one face of the transparent electric conductive film, and the polarizing plate is preferably laminated on a face of the base material on the reverse side of the face where the transparent conductive film is overlaid.

The polarizing plate may be either a circularly polarizing plate, or a linearly polarizing plate, and in a case where the composite is used for a touchscreen, a circularly polarizing plate is preferably used for improving the visibility of the same.

The circularly polarizing plate preferably includes one linearly polarizing plate, and one or two or more retardation plate(s). The process for laminating the polarizing plate and the transparent electric conductive film is not particularly limited, and the lamination may be executed by using an adhesive or the like which does not impair the effects of the embodiment of the present invention, and properties as a touchscreen, and the like.

Color Filter Substrate

The color filter substrate includes a colored part on at least one face of the base material.

The colored part may be formed on the base material by a conventionally well-known method.

The procedure of forming the colored part on the base material may be, for example, as in the following.

Specifically, the surface of the base material is first cleaned.

Next, a film is formed on one face of the base material by using a black matrix material such as chromium or a black resin by a sputtering process, or the like. Subsequently, a photoresist material or the like is coated on the surface of the film of the black matrix material, and is dried as needed, followed by an exposure with a photomask, and development to permit patterning of the resist.

Thereafter, etching, and separation of the resist are conducted to leave the black matrix material only on the necessary portion. Then, a heat treatment is carried out to allow for hardening, whereby a black matrix can be formed. The temperature in the heat treatment may be properly regulated depending on the material employed, and is preferably 150° C. to 300° C., more preferably 180° C. to 250° C., and still more preferably 220° C. to 250° C.

Then, colored parts of each color such as red, green and blue (RGB) are formed. For example, when a red colored part is formed, a red coloring matter material is applied and prebaked to obtain a red coloring matter material film. Subsequently, a photoresist is coated on the surface of the red coloring matter material film, and is dried as needed, followed by an exposure with a photomask, and development to permit patterning of the resist.

Thereafter, etching, and separation of the resist are conducted to leave the red coloring matter material only on the necessary portion. Then, a heat treatment is carried out to allow for hardening, whereby a red colored part is formed. The temperature in the heat treatment may be properly regulated depending on the material employed, and is preferably 150° C. to 300° C., more preferably 180° C. to 250° C., and still more preferably 220° C. to 250° C. A colored part of other each color such as green or blue may be also formed by repeating a similar operation.

Alternatively, colored parts of each color may be formed through concomitantly applying the coloring matter materials having each color such as red, green or blue (RGB) on the black matrix according to a similar process.

Since the base material has superior heat resistance, the black matrix material, and coloring matter materials of each color can be sufficiently hardened. Thus, a color filter substrate having a high contrast and a high definition can be produced.

As a patterning method of the black matrix and colored parts of each color, not only the procedure carried out using the photoresist described above, but also a procedure in which direct patterning is carried out through a photomask by using a photosensitive black matrix material and coloring matter materials of each color without using a resist may be adopted. Alternatively, direct patterning of the black matrix and/or the colored parts of each color can be executed according to a printing process such as screen printing, gravure printing or ink jet printing.

It is to be noted that as the black matrix material and the coloring matter materials of each color, a mixture of: a metal such as chromium, or a black material such as carbon black; a coloring matter that expresses red, green or blue; and an acrylic resin, an epoxy resin, a polyimide resin or the like may be used.

As the photoresist material, a mixture of a resin such as an acrylic resin, an epoxy resin or a polyimide resin with arbitrary additive(s) may be used. In light of coating properties, these black matrix material, coloring matter materials of each color and photoresist material are preferably used in a solution prepared by appropriately adding a solvent or the like that does not dissolve the base material.

Next, for the purpose of planarization and protection of the surface of the colored part, an overcoat layer may be also formed on the surface of the colored part as needed. For the overcoat layer, a curable resin, principally an epoxy or acrylic resin, may be used and the thickness is typically 1 µm to 10 µm.

In addition, a transparent conductive film constituted with a well-known metal oxide film may be formed on the colored part and/or the overcoat layer as needed. For example, a metal oxide film constituted with: indium oxide, cadmium oxide or tin oxide doped with tin, tellurium, cadmium, molybdenum, tungsten, zinc, germanium or an oxide of the same, etc., as an impurity; zinc oxide doped with aluminum as an impurity; titanium oxide; or the like may be exemplified. Of these, a transparent conductive film constituted with indium oxide containing 2% by mass to 15% by mass tin oxide is preferably used owing to superior transparency and electric conductivity. The film thickness of the transparent conductive film may be predetermined according to intended surface resistance, and is preferably 5 nm to 10 µm. These transparent conductive films may be overlaid on the colored part and/or the overcoat layer by a sputtering process, a vacuum deposition process, an ion plating process, a plasma CVD process or the like.

In order to adjust the specific resistance of the transparent conductive film to be no greater than $1 \times 10^{-3}$ $\Omega \cdot cm$, the temperature of the base material in providing the transparent conductive film on the base material is preferably 20° C. to 400° C., and more preferably 180° C. to 350° C.

Switching Element Substrate

The switching element substrate includes a switching element on at least one face of the base material.

The switching element is not particularly limited, and a thin film transistor (TFT) element, an MIM (Metal Insulator Metal) element, and the like may be exemplified. Of these, a TFT element is preferred in light of superior switching performance.

The TFT element is not particularly limited, and for example, a TFT element composed of a gate electrode, a source electrode, a drain electrode and an active layer may be exemplified, and may be produced by a conventionally well-known method.

The process for forming the TFT element on the base material is exemplified by a process involving, for example, the following (1) to (5), and the like.

(1) A gate electrode is provided on the base material through forming a film constituted with an electrically conductive material such as a metal or a metal oxide, etc., by a sputtering process or the like, followed by etching, etc. The temperature in forming the film constituted with a metal or a metal oxide by a sputtering process or the like is preferably 150° C. to 350° C., more preferably 180° C. to 300° C., and still more preferably 220° C. to 260° C.

(2) Next, on the base material provided with the gate electrode, a gate insulating film such as a silicon nitride film is formed by a plasma CVD process or the like.

(3) Further, on the gate insulating film, an active layer constituted with an organic semiconductor or the like is formed by a plasma CVD process or the like.

The temperature in forming the gate insulating film, the film of an organic semiconductor or the like by a plasma CVD process or the like is preferably 150° C. to 350° C., more preferably 180° C. to 300° C., and still more preferably 220° C. to 260° C.

(4) Next, a source electrode and a drain electrode are provided on the active layer, through forming a film constituted with an electrically conductive material such as a metal or a metal oxide by a sputtering process or the like followed by etching, etc.

(5) Finally, as needed, a silicon nitride film or the like is formed on the source electrode and/or the drain electrode by a plasma CVD process or the like to give a protective film. Accordingly, a TFT element can be formed.

In the foregoing process, a bottom gate type TFT element has been explained; however, the TFT element is not limited to this structure, and a top gate type may be also adopted.

Since the base material has superior heat resistance, the gate electrode, the source electrode, the drain electrode, the active layer and the like can be formed at the aforementioned temperatures desired. Thus, a switching element substrate having high resolution, detailed expression of gradation, a high contrast and a high definition can be produced.

The gate electrode, the source electrode and the drain electrode are not particularly limited as long as they are formed from the electrically conductive material. The electrically conductive material is exemplified by a metal, a metal oxide, and the like.

Examples of the metal include platinum, gold, silver, nickel, chromium, copper, iron, tin, antimony lead, tantalum, indium, aluminum, zinc, magnesium, and alloys of these, and the like, whereas examples of the metal oxide include ITO, IZO, ZnO, In—Ga—$ZnO_4$, $In_2O_3$, and the like.

In addition thereto, taking into consideration the adhesiveness to the base material, an electrically conductive polymer may be used as the electrically conductive material.

Of these, use of a metal oxide is preferred, since the transparent electrode can be formed.

The active layer may be formed from an arbitrary material, and a material having a high relative permittivity, and a low electric conductivity is preferred. Examples of the material for forming such an active layer include: inorganic semiconductors such as amorphous silicon, polycrystalline silicon, CdS, GaS, ZnS, CdSe, CaSe, ZnSe, CdTe, SiC and Si; and organic semiconductors such as polythiophene and derivatives thereof, polyparaphenylene vinylene and derivatives thereof, polyparaphenylene and derivatives thereof, polyfluorene and derivatives thereof, polythiophene vinylene and derivatives thereof, polythiophene-heterocyclic aromatic copolymers and derivatives thereof, oligoacenes such as pentacene, tetracene and naphthalene and derivatives thereof, oligothiophene such as α-6-thiophene and α-5-thiophene and derivatives thereof, phthalocyanine and derivatives thereof, pyromellitic acid dianhydride or pyromellitic acid diimide and derivatives thereof, and perylene tetracarboxylic acid dianhydride or perylene tetracarboxylic acid diimide and derivatives thereof.

For forming the gate insulating film, an inorganic substance and/or an organic substance may be used. Examples of the inorganic substance include $Si_3N_4$, $SiO_2$, SiNx, $Al_2O_3$, $TiO_2$, $Ta_2O_5$, $HfO_2$, $ZrO_2$, BST (barium strontium titanate), PZT (lead titanate zirconate) and the like, and examples of the organic substance include generally versatile polymers (methyl polymethacrylate resins, polystyrene resins), polymeric derivatives having a phenol group, acrylic polymers, imide polymers, aryl ether polymers, amide polymers, fluorine polymers, vinyl alcohol polymers and blended matters of these, and the like. Also, as the gate insulating film, an inorganic-organic laminated film may be used.

It is to be noted that on a face of the base material on the reverse side of the face where the TFT element is formed, a barrier layer may be provided in order to inhibit infiltration of the moisture into the TFT element through the base material.

The barrier layer is not particularly limited, and a composite layer including an inorganic substance layer and a polymer layer may be exemplified.

Exemplary inorganic substance layer include a layer constituted with a metal oxide, a metal nitride, a metal carbide a metaloxy nitride or the like. Examples of the metal oxide include silica, alumina, titania, indium oxide, tin oxide, indium tin oxide, and the like. Examples of the metal nitride include aluminum nitride, silicon nitride, and the like. Examples of the metal carbide include silicon carbide, and the like. Examples of the metaloxy nitride include silicon acid nitride, and the like. Such an inorganic substance layer can be formed by a vapor deposition process.

The MIM element is not particularly limited as long as it is a diode in which an insulating layer is provided between metals, and may be produced by a conventionally well-known method.

The process for forming the MIM element on the base material is exemplified by a process involving, for example, the following (1) to (3).

(1) An electrode is provided on the base material through forming a film constituted with a metal, a metal oxide, etc., by a sputtering process or the like, followed by etching, etc.
(2) Next, on the base material provided with the electrode, an insulating layer such as a silicon nitride film is formed by a plasma CVD process or the like. (3) Next, an electrode is provided on the insulating layer, through forming a film of a metal, a metal oxide, etc., by a sputtering process or the like, followed by etching, etc.

Examples of the metal include platinum, gold, silver, nickel, chromium, copper, iron, tin, antimony lead, tantalum, indium, aluminum, zinc, magnesium, and alloys of these, whereas examples of the metal oxide include ITO, IZO, ZnO, $In_2O_3$, and the like. Otherwise, taking into consideration the adhesiveness to the base material, an electrically conductive polymer may be used as the electrically conductive material.

Of these, use of a metal oxide is preferred, since the transparent electrode can be formed.

EXAMPLES

Hereinafter, the embodiments of the present invention will be explained in more detail by way of Examples, but the present invention is not in any way limited by Examples. Each physical property value was determined according to the method described below.
Weight Average Molecular Weight The polystyrene equivalent weight average molecular weight (Mw) of the compound (A) was determined by gel permeation chromatography (detector: differential refractometer) using GPC columns (G2000HXL×2, G3000HXL×1) manufactured by Tosoh Corporation and monodisperse polystyrenes as a standard under analytical conditions involving the flow rate of 1.0 mL/min, the elution solvent of tetrahydrofuran and the column temperature of 40° C.
Film Thickness The film thickness was determined by using a spectroscopic ellipsometer (M2000D, manufactured by J. A. WOOLLAM).
Synthesis of Compound (A)

The compounds used in the synthesis of the compound (A) are shown below.

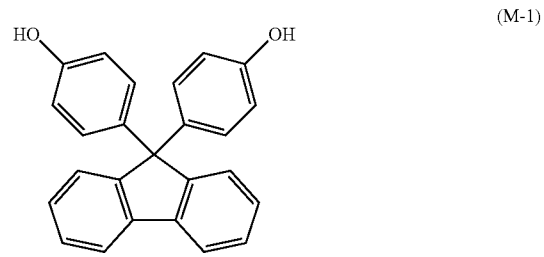

(M-1)

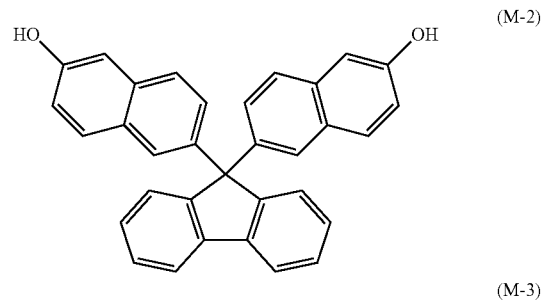

(M-2)

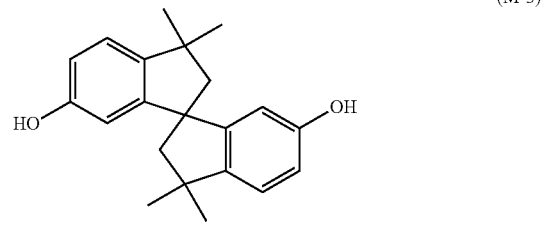

(M-3)

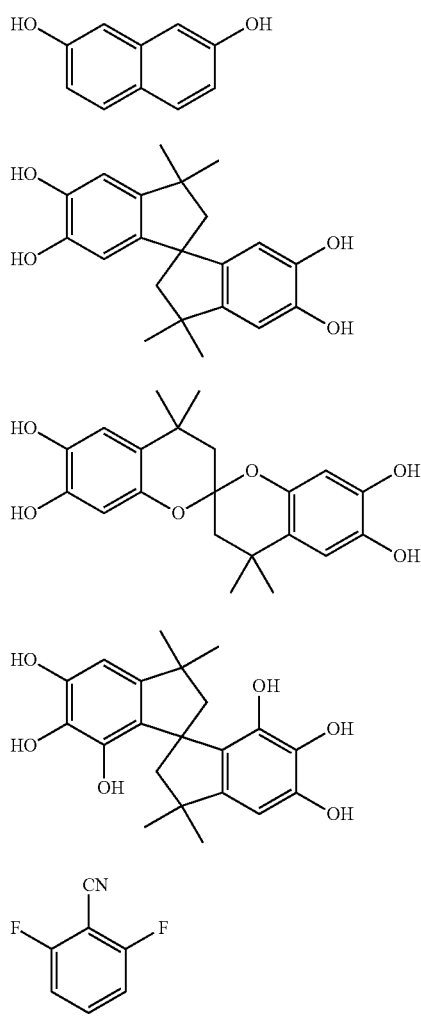

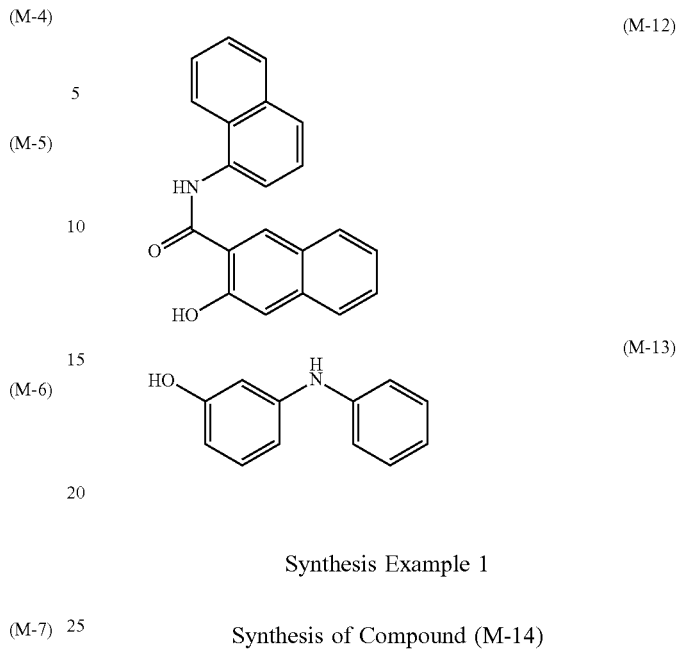

Synthesis of Compounds (A1)
Synthesis of Precursor: Synthesis of (M-14) to (M-18)

The compounds used in the synthesis of precursors of the compound (A1) are shown below.

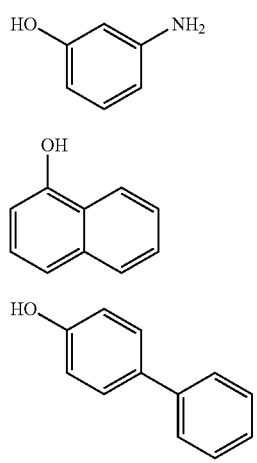

Synthesis Example 1

Synthesis of Compound (M-14)

Into a separable flask equipped with a thermometer, 88 parts by mass of the compound (M-9) and 112 parts by mass of the compound (M-8), 111 parts by mass of potassium carbonate as a basic compound, and 806 parts by mass of dimethylacetamide as a solvent were charged in a nitrogen atmosphere, and thereafter a reaction was allowed at 100° C. for 4 hrs with stirring. The resulting reaction mixture was filtered, and thereafter methanol and water were added to permit reprecipitation. The resultant precipitates were dried to obtain a compound represented by the following formula (M-14).

Synthesis Examples 2 to 5

Synthesis of Compounds (M-15) to (M-18)

Similarly to Synthesis Example 1 except that the compounds (M-10) to (M-13) were used, respectively, in place of the compound (M-9) in Synthesis Example 1, compounds represented by the following formulae (M-15) to (M-18) were each obtained.

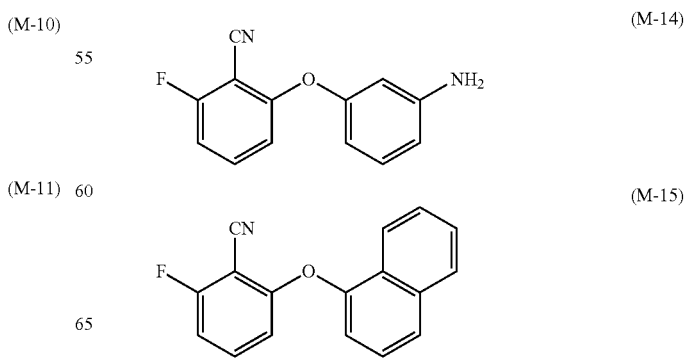

-continued

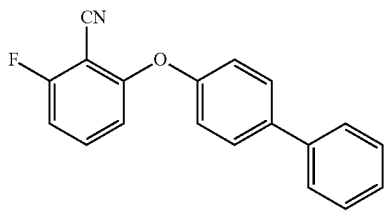
(M-16)

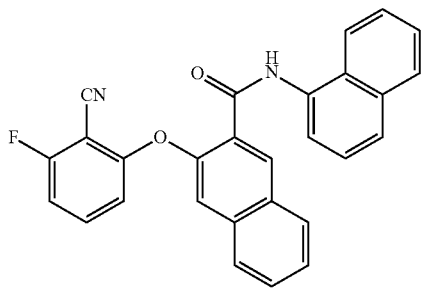
(M-17)

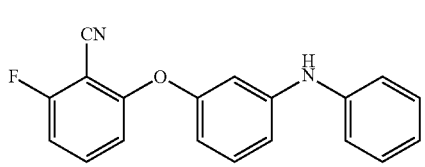
(M-18)

Synthesis of Compound (A1)

Example 1

Synthesis of Compound (A1-1)

Into a separable flask equipped with a thermometer, 68 parts by mass of the compound (M-5) and 192 parts by mass of the compound (M-14) (molar ratio of (M-14) to (M-5) being 4.2), 111 parts by mass of potassium carbonate as the basic compound, and 1,042 parts by mass of dimethylacetamide as the solvent were charged in a nitrogen atmosphere, and thereafter a reaction was allowed at 100° C. for 4 hrs with stirring. The resulting reaction mixture was filtered, and thereafter methanol was added to permit reprecipitation. The resultant precipitates were dried to obtain a compound represented by the following formula (A1-1). The compound (A1-1) had an Mw of 1,200.

Example 2

Synthesis of Compound (A1-2)

Into a separable flask equipped with a thermometer, 61 parts by mass of the compound (M-5) and 199 parts by mass of the compound (M-15) (molar ratio of (M-15) to (M-5) being 4.2), 99 parts by mass of potassium carbonate as the basic compound, and 936 parts by mass of dimethylacetamide as the solvent were charged in a nitrogen atmosphere, and thereafter a reaction was allowed at 100° C. for 4 hrs with stirring. The resulting reaction mixture was filtered, and thereafter methanol was added to permit reprecipitation. The resultant precipitates were dried to obtain a compound represented by the following formula (A1-2). The compound (A1-2) had an Mw of 1,300.

Example 3

Synthesis of Compound (A1-3)

Into a separable flask equipped with a thermometer, 57 parts by mass of the compound (M-5) and 203 parts by mass of the compound (M-16) (molar ratio of (M-16) to (M-5) being 4.2), 92 parts by mass of potassium carbonate as the basic compound, and 870 parts by mass of dimethylacetamide as the solvent were charged in a nitrogen atmosphere, and thereafter a reaction was allowed at 100° C. for 4 hrs with stirring. The resulting reaction mixture was filtered, and thereafter methanol was added to permit reprecipitation. The resultant precipitates were dried to obtain a compound represented by the following formula (A1-3). The compound (A1-3) had an Mw of 1,400.

Example 4

Synthesis of Compound (A1-4)

Into a separable flask equipped with a thermometer, 41 parts by mass of the compound (M-5) and 219 parts by mass of the compound (M-17) (molar ratio of (M-17) to (M-5) being 4.2), 67 parts by mass of potassium carbonate as the basic compound, and 628 parts by mass of dimethylacetamide as the solvent were charged in a nitrogen atmosphere, and thereafter a reaction was allowed at 100° C. for 4 hrs with stirring. The resulting reaction mixture was filtered, and thereafter methanol was added to permit reprecipitation. The resultant precipitates were dried to obtain a compound represented by the following formula (A1-4). The compound (A1-4) had an Mw of 2,000.

Example 5

Synthesis of Compound (A1-5)

Into a separable flask equipped with a thermometer, 55 parts by mass of the compound (M-5) and 205 parts by mass of the compound (M-18) (molar ratio of (M-18) to (M-5) being 4.2), 89 parts by mass of potassium carbonate as the basic compound, and 836 parts by mass of dimethylacetamide as the solvent were charged in a nitrogen atmosphere, and thereafter a reaction was allowed at 100° C. for 4 hrs with stirring. The resulting reaction mixture was filtered, and thereafter methanol was added to permit reprecipitation. The resultant precipitates were dried to obtain a compound represented by the following formula (A1-5). The compound (A1-5) had an Mw of 1,500.

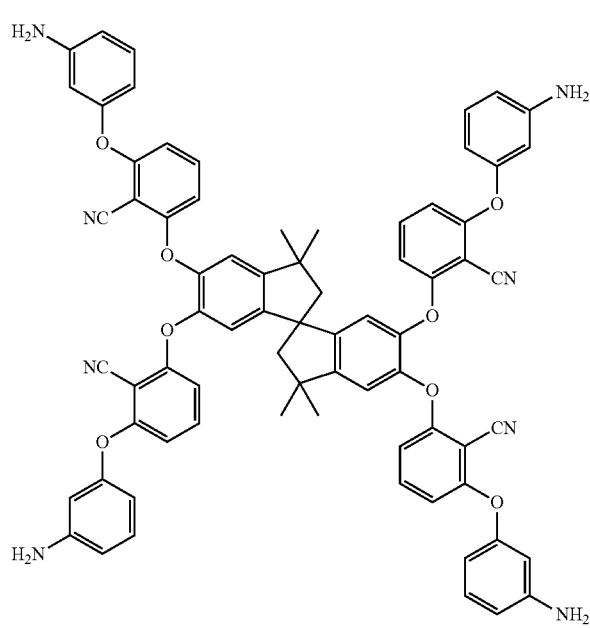
(A1-1)
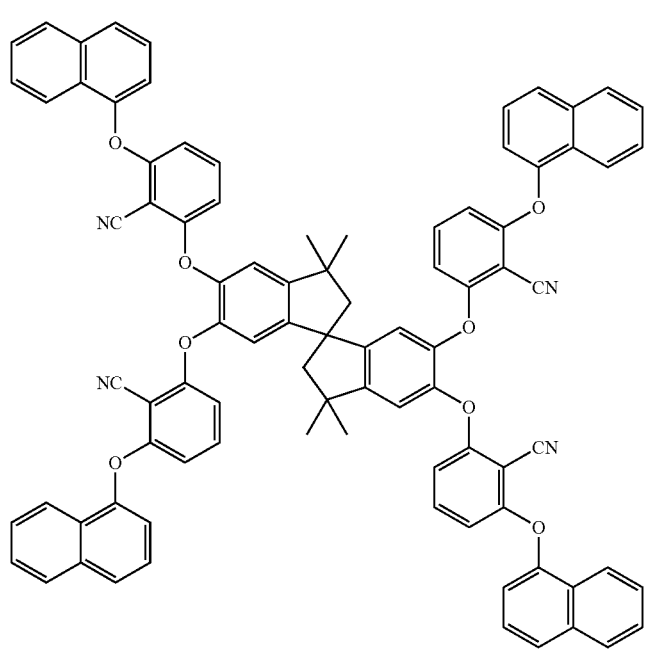
(A1-2)

(A1-3)
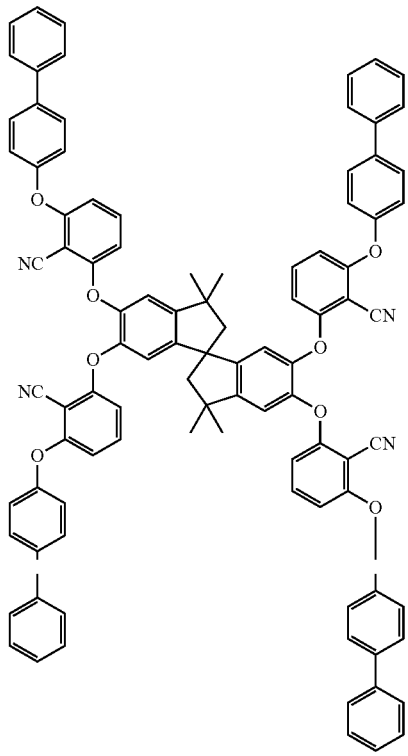
(A1-4)
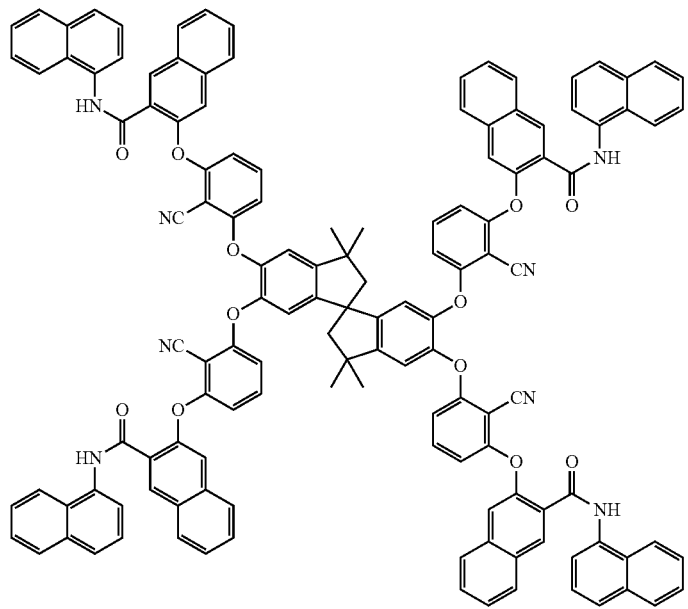

(A1-5)

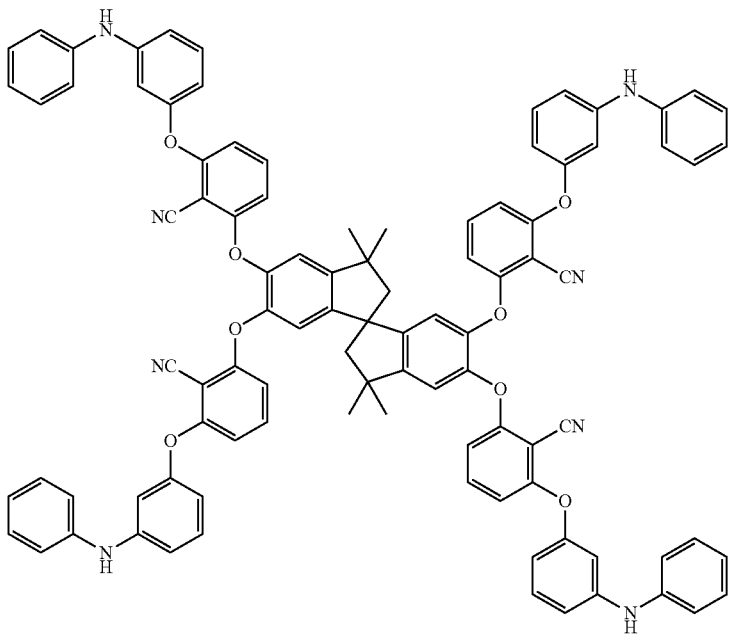

Synthesis of Polymers (A2)

Example 6

Synthesis of Polymer (A2-1)

Into a separable flask equipped with a thermometer, 174 parts by mass of the compound (M-1) (54 mol %), 13 parts by mass of the compound (M-5) (4 mol %) and 53 parts by mass of the compound (M-8) (42 mol %), 79 parts by mass of potassium carbonate as the basic compound, and 459 parts by mass of dimethylacetamide as the solvent were charged in a nitrogen atmosphere, and thereafter a condensation polymerization reaction was allowed at 140° C. for 4 hrs with stirring. The resulting reaction mixture was filtered, and thereafter methanol was added to permit reprecipitation. The resultant precipitates were dried to obtain a polymer having a structure represented by the following formula (A2-1). The polymer (A2-1) had an Mw of 4,500.

Example 7

Synthesis of Polymer (A2-2)

Into a separable flask equipped with a thermometer, 185 parts by mass of the compound (M-2) (54 mol %), 11 parts by mass of the compound (M-5) (4 mol %) and 44 parts by mass of the compound (M-8) (42 mol %), 65 parts by mass of potassium carbonate as the basic compound, and 379 parts by mass of dimethylacetamide as the solvent were charged in a nitrogen atmosphere, and thereafter a condensation polymerization reaction was allowed at 140° C. for 4 hrs with stirring. The resulting reaction mixture was filtered, and thereafter methanol was added to permit reprecipitation. The resultant precipitates were dried to obtain a polymer having a structure represented by the following formula (A2-2). The polymer (A2-2) had an Mw of 5,000.

Example 8

Synthesis of Polymer (A2-3)

Into a separable flask equipped with a thermometer, 168 parts by mass of the compound (M-3) (54 mol %), 14 parts by mass of the compound (M-5) (4 mol %) and 58 parts by mass of the compound (M-8) (42 mol %), 87 parts by mass of potassium carbonate as the basic compound, and 502 parts by mass of dimethylacetamide as the solvent were charged in a nitrogen atmosphere, and thereafter a condensation polymerization reaction was allowed at 140° C. for 4 hrs with stirring. The resulting reaction mixture was filtered, and thereafter methanol was added to permit reprecipitation. The resultant precipitates were dried to obtain a polymer having a structure represented by the following formula (A2-3). The polymer (A2-3) had an Mw of 4,000.

Example 9

Synthesis of Polymer (A2-4)

Into a separable flask equipped with a thermometer, 131 parts by mass of the compound (M-4) (54 mol %), 21 parts by mass of the compound (M-5) (4 mol %) and 88 parts by mass of the compound (M-8) (42 mol %), 130 parts by mass of potassium carbonate as the basic compound, and 756 parts by mass of dimethylacetamide as the solvent were charged in a nitrogen atmosphere, and thereafter a condensation polymerization reaction was allowed at 140° C. for 4 hrs with stirring. The resulting reaction mixture was filtered, and thereafter methanol was added to permit reprecipitation. The resultant precipitates were dried to obtain a polymer having a structure represented by the following formula (A2-4). The polymer (A2-4) had an Mw of 3,500.

Example 10

Synthesis of Polymer (A2-5)

Into a separable flask equipped with a thermometer, 173 parts by mass of the compound (M-1) (54 mol %), 14 parts by mass of the compound (M-6) (4 mol %) and 53 parts by mass of the compound (M-8) (42 mol %), 79 parts by mass of potassium carbonate as the basic compound, and 456 parts by mass of dimethylacetamide as the solvent were charged in a nitrogen atmosphere, and thereafter a condensation polymerization reaction was allowed at 140° C. for 4 hrs with stirring. The resulting reaction mixture was filtered, and thereafter methanol was added to permit reprecipitation. The resultant precipitates were dried to obtain a polymer having a structure represented by the following formula (A2-5). The polymer (A2-5) had an Mw of 4,500.

Example 11

Synthesis of Polymer (A2-6)

Into a separable flask equipped with a thermometer, 180 parts by mass (56 mol %) of the compound (M-1), 7 parts by mass (2 mol %) of the compound (M-7) and 53 parts by mass (42 mol %) of the compound (M-8), 79 parts by mass of potassium carbonate as the basic compound, and 457 parts by mass of dimethylacetamide as the solvent were charged in a nitrogen atmosphere, and thereafter a condensation polymerization reaction was allowed at 140° C. for 4 hrs with stirring. The resulting reaction mixture was filtered, and thereafter methanol was added to permit reprecipitation. The resultant precipitates were dried to obtain a polymer having a structure represented by the following formula (A2-6). The polymer (A2-6) had an Mw of 5,500.

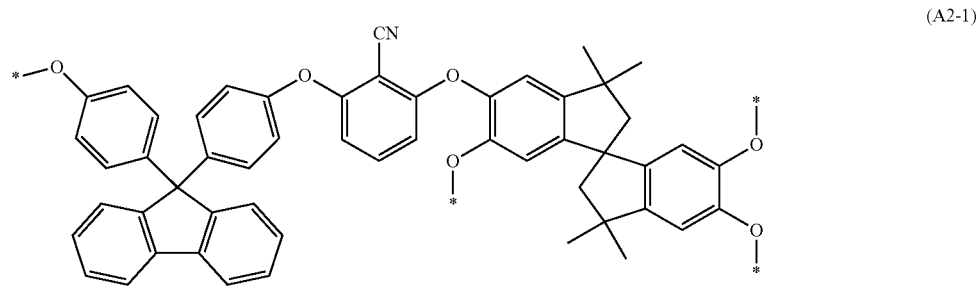

(A2-1)

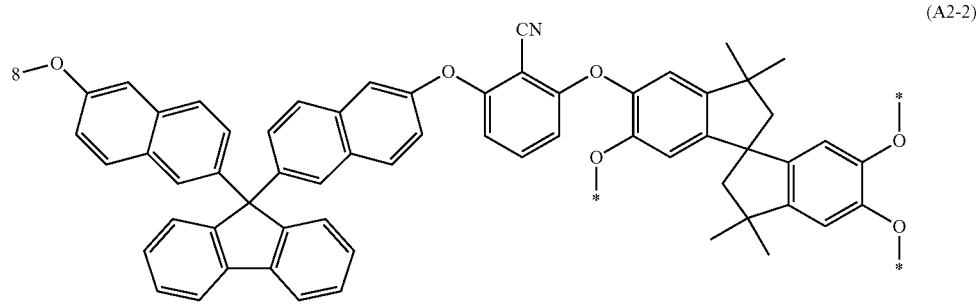

(A2-2)

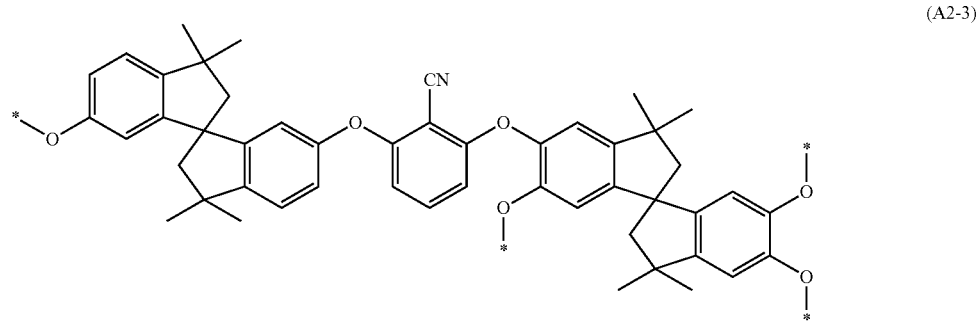

(A2-3)

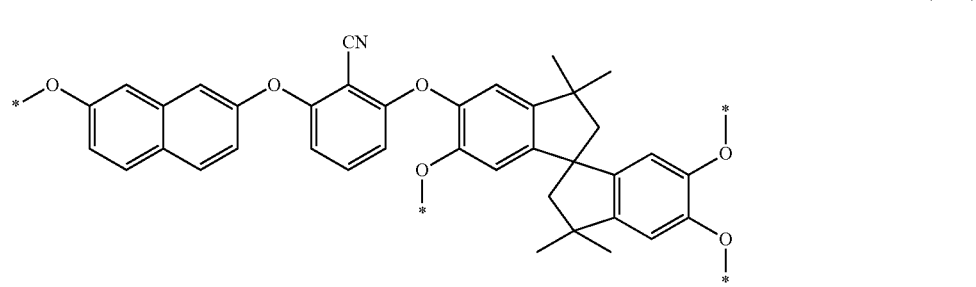

(A2-4)

-continued

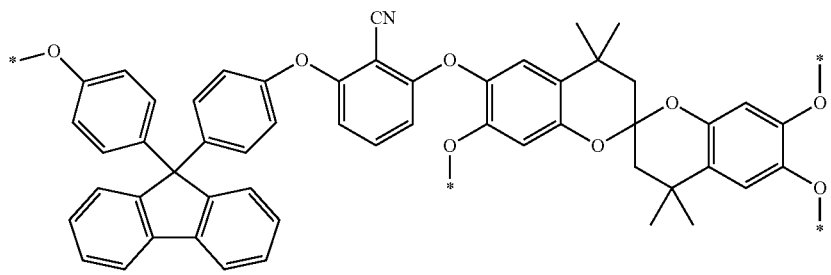

(A2-5)

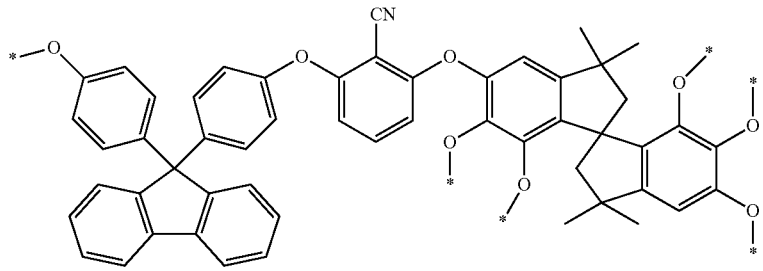

(A2-6)

In the above formulae (A2-1) to (A2-6), * represents an atomic bonding.

Example 12

Synthesis of Polymer (A2-7)

Into a separable flask equipped with a thermometer, a condenser and a Dean-Stark tube, 44.1 parts by mass (33.2 mol %) of the compound (M-1), 64.4 parts by mass (33.2 mol %) of the compound (M-2), 20.2 parts by mass (33.6 mol %) of the compound (M-3), 41 parts by mass of potassium carbonate as the alkali metal compound, and 235 parts by mass of N,N-dimethylacetamide as the solvent, 25 parts by mass of toluene as an azeotropic dehydrating solvent were charged in a nitrogen atmosphere, and thereafter a condensation polymerization reaction was allowed at 120° C. for 4 hrs with stirring. The resulting reaction mixture was filtered, and thereafter methanol was added to permit reprecipitation. The resultant precipitates were dried to obtain a white powder polymer (A2-7) which is a random copolymer having a structure represented by the following formula (P-1) and a structure represented by the following formula (P-2). The polymer (A2-7) had an Mw of 3,900.

Example 13

Synthesis of Polymer (A2-8)

Similarly to Synthesis Example 12 except that 44.1 parts by mass (33.2 mol %) of the compound (M-1), 47 parts by mass (33.2 mol %) of the compound (M-4) and 20.2 parts by mass (33.6 mol %) of the compound (M-3) were used as the monomer compound, and the time period of the condensation polymerization reaction in Example 12 was changed to 2 hrs, a white powder polymer (A2-8) which is a random copolymer having a structure represented by the following formula (P-1) and a structure represented by the following formula (P-3) was obtained. The polymer (A2-8) had an Mw of 3,100.

Example 14

Synthesis of Polymer (A2-9)

Similarly to Synthesis Example 12 except that 44.1 parts by mass (33.2 mol %) of the compound (M-1), 49.8 parts by mass (33.2 mol %) of the compound (M-5) and 20.2 parts by mass (33.6 mol %) of the compound (M-3) were used as the monomer compound, and the time period of the condensation polymerization reaction in Example 12 was changed to 2 hrs, a white powder polymer (A2-9) which is a random copolymer having a structure represented by the following formula (P-1) and a structure represented by the following formula (P-4) was obtained. The polymer (A2-9) had an Mw of 3,500.

Example 15

Synthesis of Polymer (A2-10)

Similarly to Synthesis Example 12 except that 44.1 parts by mass (33.2 mol %) of the compound (M-1), 45.5 parts by mass (33.2 mol %) of the compound (M-6) and 20.2 parts by mass (33.6 mol %) of the compound (M-3) were used as the monomer compound, and the time period of the condensation polymerization reaction in Example 12 was changed to 3 hrs, a white powder polymer (A2-10) which is a random copolymer having a structure represented by the following formula (P-1) and a structure represented by the following formula (P-5) was obtained. The polymer (A2-10) had an Mw of 2,900.

Example 16

Synthesis of Polymer (A2-11)

Similarly to Synthesis Example 12 except that 44.1 parts by mass (33.2 mol %) of the compound (M-1), 55 parts by mass (33.2 mol %) of the compound (M-7) and 20.2 parts by mass (33.6 mol %) of the compound (M-3) were used as the monomer compound, and the time period of the condensation polymerization reaction in Example 12 was changed to 2 hrs, a white powder polymer (A2-11) which is a random copolymer having a structure represented by the following formula (P-1) and a structure represented by the following formula (P-6) was obtained. The polymer (A2-11) had an Mw of 2,700.

Example 17

Synthesis of Polymer (A2-12)

Similarly to Synthesis Example 12 except that 44.1 parts by mass (33.2 mol %) of the compound (M-1), 35.8 parts by mass (33.2 mol %) of the compound (M-8) and 20.2 parts by mass (33.6 mol %) of the compound (M-3) were used as the monomer compound, and the time period of the condensation polymerization reaction in Example 12 was changed to 2 hrs, a white powder polymer (A2-12) which is a random copolymer having a structure represented by the following formula (P-1) and a structure represented by the following formula (P-7) was obtained. The polymer (A2-12) had an Mw of 5,400.

Example 18

Synthesis of Polymer (A2-13)

Similarly to Synthesis Example 12 except that 44.1 parts by mass (33.2 mol %) of the compound (M-1), 50.1 parts by mass (33.2 mol %) of the compound (M-9) and 20.2 parts by mass (33.6 mol %) of the compound (M-3) were used as the monomer compound, and the time period of the condensation polymerization reaction in Example 12 was changed to 3 hrs, a white powder polymer (A2-13) which is a random copolymer having a structure represented by the following formula (P-1) and a structure represented by the following formula (P-8) was obtained. The polymer (A2-13) had an Mw of 3,100.

(P-1)

(P-2)

(P-3)
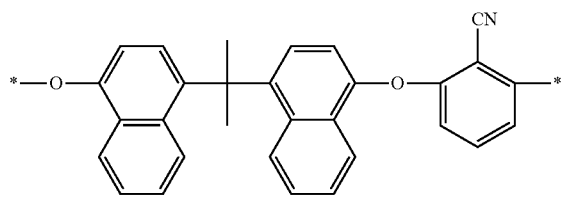

(P-4)
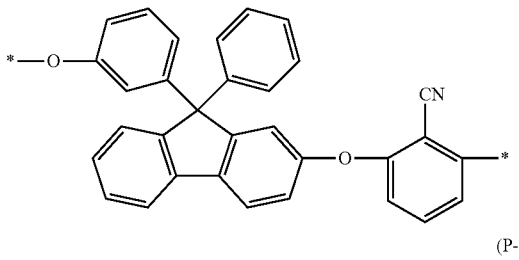

(P-5)
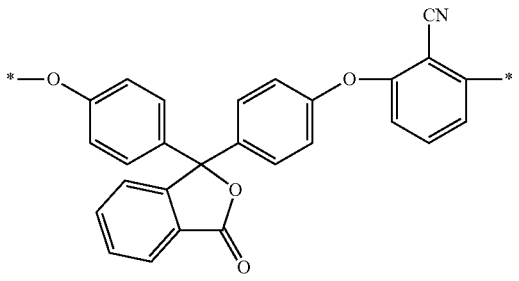

(P-6)
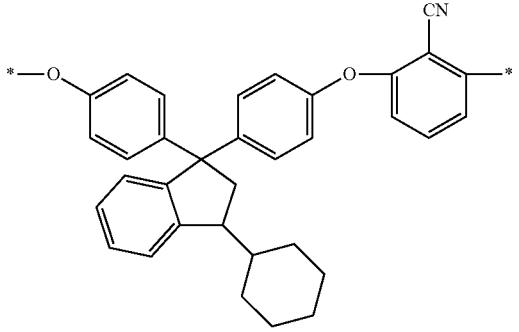

(P-7)
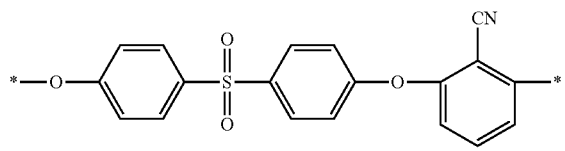

(P-8)
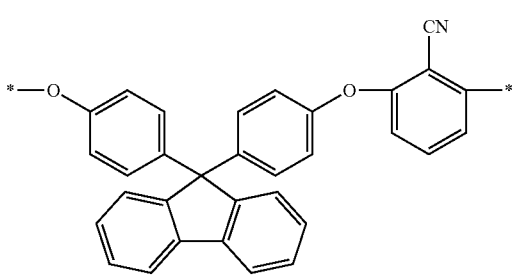

In the above formulae (P-1) to (P-8), * represents an atomic bonding.

Synthesis Example 6

Synthesis of Polymer (a2-1)

Into a separable flask equipped with a thermometer, 187 parts by mass of the compound (M-1) and 53 parts by mass of the compound (M-8), 74 parts by mass of potassium carbonate as the basic compound, and 458 parts by mass of dimethylacetamide as the solvent were charged in a nitrogen atmosphere, and thereafter a condensation polymerization reaction was allowed at 140° C. for 4 hrs with stirring. The resulting reaction mixture was filtered, and thereafter methanol was added to permit reprecipitation. The resultant precipitates were dried to obtain a polymer having a structure represented by the following formula (a2-1). The polymer (a2-1) had an Mw of 4,000.

Synthesis Example 7

Synthesis of Polymer (a2-2)

Into a separable flask equipped with a thermometer, 100 parts by mass of 2,7-dihydroxynaphthalene, 30 parts by mass of formalin and 1 part by mass of p-toluenesulfonic acid, and 150 parts by mass of propylene glycol monomethyl ether as the solvent were charged in a nitrogen atmosphere, and thereafter a polymerization reaction was allowed at 80° C. for 6 hrs with stirring. The resulting polymerization reaction mixture was diluted with 100 parts by mass of n-butyl acetate, and the organic layer was washed with a large quantity of a mixed solvent containing water and methanol (mass ratio of water to methanol: 1/2). The solvent was distilled off from the organic layer thus obtained to obtain a polymer having a structure represented by the following formula (a2-2). The polymer (a2-2) had an Mw of 1,800.

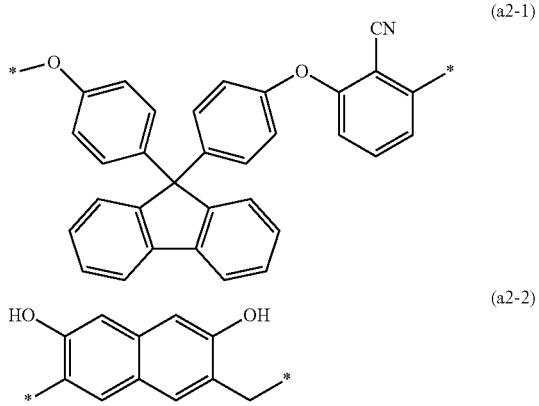

(a2-1)

(a2-2)

In the above formulae (a2-1) and (a2-2), * represents an atomic bonding.

Preparation of Compositions

Each component other than the compounds (A) used in the preparation of the compositions is shown below.

(B) Solvent
B-1: propylene glycol monomethyl ether acetate
B-2: cyclohexanone
B-3: ethyl lactate
B-4: γ-butyrolactone
B-5: methyl n-amyl ketone (C) Acid Generating Agent
C-1: bis(4-t-butylphenyl)iodonium nonafluoro-n-butane-sulfonate (a compound represented by the following formula (C-1))

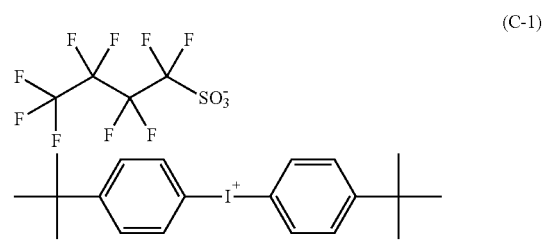

(C-1)

(D) Crosslinking Agent
D-1: Nikalac N-2702 (manufactured by Sanwa Chemical Co., Ltd) (a compound represented by the following formula (D-1))
D-2: 4,4'-(1-(4-(1-(4-hydroxy-3,5-bis(methoxymethyl)phenyl)-1-methylethyl)phenyl)ethylidene)bis(2,6-bis(methoxymethyl)phenol) (a compound represented by the following formula (D-2))
D-3: a compound represented by the following formula (D-3) (random copolymer of acenaphthylene and hydroxymethylacenaphthylene; proportion of repeating unit derived from acenaphthylene/repeating unit derived from hydroxymethyl acenaphthylene: 50/50 (mol %); Mw: 1,500; synthesized with reference to Japanese Unexamined Patent Application, Publication No. 2004-168748)

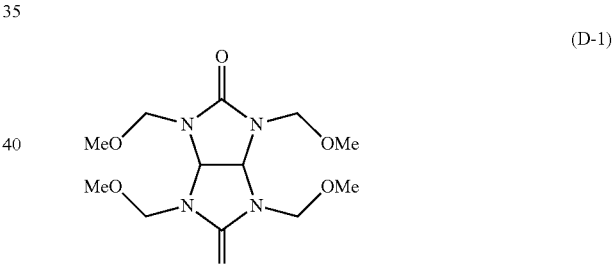

(D-1)

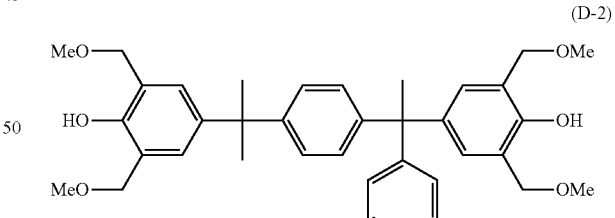

(D-2)

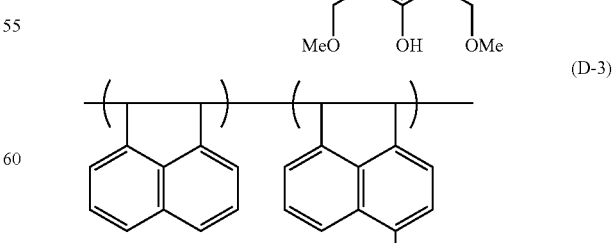

(D-3)

Example 19

A solution was obtained by mixing 10 parts by mass of (A1-1) as the compound (A1), and 100 parts by mass of (B-1) as the solvent (B). The resulting solution was filtered through a membrane filter having a pore size of 0.1 μm to prepare a composition (J1-1).

Examples 20 to 42, and Comparative Examples 1 to 3

Compositions (J1-2) to (J1-9), (J2-1) to (J2-15), and (CJ2-1) to (CJ2-3) were prepared in a similar manner to Example 19 except that the type and the amount of each component blended were as specified in Tables 1-1 and 1-2. In Tables 1-1 and 1-2, "-" indicates that the corresponding component was not used.

(unfavorable) in a case where the turbidity and/or precipitation was found in the solution.

Optical Characteristics (Refractive Index and Extinction Coefficient)

The composition obtained as described above was spin-coated on the surface of a silicon wafer having a diameter of 8 inches, and thereafter heated at 350° C. for 2 min to form a film having a thickness of 250 nm. Then, a refractive index and an extinction coefficient at a wavelength of 193 nm of the film thus formed were measured using a spectroscopic ellipsometer (M2000D, manufactured by J. A. WOOL-LAM). Each measurement value is shown in Table 2. The optical characteristics can be evaluated as being: favorable in a case where the refractive index fell within a range of no less than 1.3 and no greater than 1.6, and the extinction coefficient fell within a range of no less than 0.2 and no greater than 0.8; and unfavorable in a case where the

TABLE 1-1

| | Composition | (A) Component type | amount (parts by mass) | (B) Solvent type | amount (parts by mass) | (C) Acid generating agent type | amount (parts by mass) | (D) Crosslinking agent type | amount (parts by mass) |
|---|---|---|---|---|---|---|---|---|---|
| Example 19 | J1-1 | A1-1 | 10 | B-1 | 100 | — | — | — | — |
| Example 20 | J1-2 | A1-2 | 10 | B-1 | 100 | — | — | — | — |
| Example 21 | J1-3 | A1-3 | 10 | B-1 | 100 | — | — | — | — |
| Example 22 | J1-4 | A1-4 | 10 | B-1 | 100 | — | — | — | — |
| Example 23 | J1-5 | A1-5 | 10 | B-1 | 100 | — | — | — | — |
| Example 24 | J1-6 | A1-1 | 10 | B-1 | 100 | C-1 | 0.5 | D-1 | 1 |
| Example 25 | J1-7 | A1-1 | 10 | B-1 | 100 | C-1 | 0.5 | D-2 | 1 |
| Example 26 | J1-8 | A1-2 | 10 | B-1 | 100 | C-1 | 0.5 | D-1 | 1 |
| Example 27 | J1-9 | A1-2 | 10 | B-1 | 100 | C-1 | 0.5 | D-2 | 1 |
| Example 28 | J2-1 | A2-1 | 10 | B-1 | 100 | — | — | — | — |
| Example 29 | J2-2 | A2-2 | 10 | B-1 | 100 | — | — | — | — |
| Example 30 | J2-3 | A2-3 | 10 | B-1 | 100 | — | — | — | — |
| Example 31 | J2-4 | A2-4 | 10 | B-1 | 100 | — | — | — | — |
| Example 32 | J2-5 | A2-5 | 10 | B-1 | 100 | — | — | — | — |
| Example 33 | J2-6 | A2-6 | 10 | B-1 | 100 | — | — | — | — |
| Example 34 | J2-7 | A2-1 | 10 | B-1 | 100 | C-1 | 0.5 | D-1 | 1 |
| Example 35 | J2-8 | A2-1 | 10 | B-1 | 100 | C-1 | 0.5 | D-2 | 1 |

TABLE 1-2

| | Composition | (A) Component type | amount (parts by mass) | (B) Solvent type | amount (parts by mass) | (C) Acid generating agent type | amount (parts by mass) | (D) Crosslinking agent type | amount (parts by mass) |
|---|---|---|---|---|---|---|---|---|---|
| Example 36 | J2-9 | A2-7 | 10 | B-1/B-2/B-3 | 50/40/10 | C-1 | 0.5 | D-3 | 1 |
| Example 37 | J2-10 | A2-8 | 10 | B-1/B-2/B-3 | 50/40/10 | C-1 | 0.5 | D-3 | 1 |
| Example 38 | J2-11 | A2-9 | 10 | B-3/B-4/B-5 | 10/10/80 | C-1 | 0.5 | D-3 | 1 |
| Example 39 | J2-12 | A2-10 | 10 | B-3/B-4/B-5 | 10/10/80 | C-1 | 0.5 | D-3 | 1 |
| Example 40 | J2-13 | A2-11 | 10 | B-1 | 100 | C-1 | 0.5 | D-3 | 1 |
| Example 41 | J2-14 | A2-12 | 10 | B-1/B-2/B-3 | 50/40/10 | C-1 | 0.5 | D-3 | 1 |
| Example 42 | J2-15 | A2-13 | 10 | B-1/B-2/B-3 | 50/40/10 | C-1 | 0.5 | D-3 | 1 |
| Comparative Example 1 | CJ2-1 | a2-1 | 10 | B-2 | 100 | — | — | — | — |
| Comparative Example 2 | CJ2-2 | a2-2 | 10 | B-2 | 100 | — | — | — | — |
| Comparative Example 3 | CJ2-3 | a2-2 | 10 | B-1 | 100 | — | — | — | — |

Evaluations

Using the composition obtained as described above, evaluations were made in regard to the items below according to the following methods. The results of the evaluations are shown in Table 2.

Solubility of Compound (A) in PGMEA

By adding the composition obtained as described above to a PGMEA (propylene glycol monomethyl ether acetate) solvent, the solubility of the compound (A) in PGMEA was evaluated. The solubility in PGMEA was evaluated as being: "A" (favorable) in a case where dissolution in the solution without turbidity and/or precipitation was achieved; and "B"

refractive index and the extinction coefficient did not fall within the respective above ranges.

Etching Resistance

The composition obtained as described above was spin-coated on a silicon wafer having a diameter of 8 inches to provide a film having a thickness of 300 nm. Thereafter, the film was subjected to an etching treatment (pressure: 0.03 Torr; high frequency power: 3000 W; Ar/CF$_4$=40/100 sccm; and substrate temperature: 20° C.), and the thickness of the film after the etching treatment was measured. Then, the etching rate (nm/min) was calculated from the relationship between a decrease of the film thickness and the treatment time, and the proportion of the etching rate of the film according to Examples with respect to that of the film according to Comparative Example 2 was calculated. The smaller value indicates more favorable etching resistance.

Heat Resistance

The composition obtained as described above was spin-coated on a silicon wafer having a diameter of 8 inches to provide a coating film, and the film thickness of the coating film was measured using the spectroscopic ellipsometer (the value of the film thickness acquired in this measurement being designated as X). Next, the film was heated at 350° C. for 120 sec, and the thickness of the film after the heating was measured using the spectroscopic ellipsometer (the value of the film thickness acquired in this measurement being designated as Y). Then, a percent decrease of the thickness of the film after the heating with respect to the thickness of the film before the heating $(100 \times (X-Y)/X)(\%)$ was calculated, and the value was defined as heat resistance. The smaller heat resistance value indicates that the film is more favorable (i.e., having superior heat resistance) as there are less sublimated matter and film degradation products generated during the heating of the film.

Flatness

The composition obtained as described above was each applied on a $SiO_2$ stepped substrate on which trenches having a width of 42 nm, a pitch of 84 nm and a depth of 180 nm (aspect ratio: 4.3), trenches having a width of 100 nm, a pitch of 150 nm and a depth of 180 nm (aspect ratio: 1.8), and trenches having a width of 5 μm and a depth of 180 nm (open spaces; aspect ratio: 0.036) were provided in combination, with the ratio of the maximum value to the minimum value in aspect ratios different from each other being 119. Thereafter, baking was carried out at 250° C. for 60 sec under an ambient air atmosphere to provide a film having a thickness of 200 nm. The shape of the film was observed using a scanning electron microscope (S-4800, manufactured by Hitachi High-Technologies Corporation), and the difference of the maximum value and the minimum value of the thickness of the film on the trenches or spaces (ΔFT) was determined. The flatness of the films shown in Table 2 below (the sum of k1 and k2 being no less than 3) was evaluated as being: "A" (favorable) in a case where the ΔFT was less than 20 nm; "B" (somewhat favorable) in a case where the ΔFT was no less than 20 nm and less than 35 nm; and "C" (unfavorable) in a case where the ΔFT was no less than 35 nm. Whereas, the flatness of the films shown in Table 3 below (each of k1 and k2 being 1) was evaluated as being: "A" (extremely favorable) in a case where the ΔFT was less than 10 nm; "B" (favorable) in a case where the ΔFT was no less than 10 nm and less than 20 nm; "C" (somewhat favorable) in a case where the ΔFT was no less than 20 nm and less than 35 nm; and "D" (unfavorable) in a case where the ΔFT was no less than 35 nm.

Solvent Resistance

A film was formed in a similar manner to the formation of the film in the evaluation of the Optical Characteristics. Then, the substrate having the film provided thereon was immersed in cyclohexanone at room temperature for 10 sec. The thickness of the film before and after the immersion was measured using the spectroscopic ellipsometer and a rate of change of the film thickness was calculated from the measurements to evaluate the solvent resistance. The solvent resistance was evaluated as being: "A" (favorable) in a case where the rate of change of the film thickness was less than 1%; "B" (somewhat favorable) in a case where the rate of change of the film thickness was no less than 1% and less than 5%; and "C" (unfavorable) in a case where the rate of change of the film thickness was no less than 5%.

Resistance to Curving

A resist underlayer film was formed in a similar manner to the formation of the resist underlayer film in the evaluation of the Optical Characteristics. Then, a solution of an intermediate layer composition for a three layer resist process (NFC SOG508, manufactured by JSR) was spin-coated on the resist underlayer film, and then heated at 200° C. for 60 sec, followed by heating at 300° C. for 60 sec to form an intermediate layer coating film having a thickness of 0.04 μm. Next, a commercially available resist composition was spin-coated on the intermediate layer coating film, and a prebaking was carried out at 100° C. for 60 sec to form a resist film having a thickness of 0.1 μm.

Next, the resist film was exposed through a mask for an optimum exposure time using an ArF immersion scanner (manufactured by NIKON, lens numerical aperture: 1.30; and exposure wavelength: 193 nm). Next, post-baking was carried out at 100° C. for 60 sec, and thereafter the resist film was developed using a 2.38% by mass aqueous tetramethylammonium hydroxide solution. Thereafter, the developed resist film was washed with water and dried to form a positive type resist pattern. Next, the intermediate layer coating film was subjected to a dry-etching treatment with a carbon tetrafluoride gas using the patterned resist film as a mask and a reactive ion etching apparatus (Telius SCCM, manufactured by Tokyo Electron Limited). When the intermediate layer coating film positioned under the opening portion of the resist film was removed, the etching treatment was stopped, resulting in the transfer of the resist pattern to the intermediate layer coating film.

Next, a dry-etching treatment with a mixed gas of oxygen and nitrogen was carried out using as a mask the intermediate layer coating film having the transferred resist pattern, and the etching apparatus. When the resist underlayer film positioned under the opening portion of the intermediate layer coating film was removed, the etching treatment was stopped, resulting in the transfer of the pattern of the intermediate layer coating film to the resist underlayer film. Next, a dry-etching treatment with a mixed gas of carbon tetrafluoride and argon was carried out with the etching apparatus, using as a mask the resist underlayer film having the pattern transferred from the intermediate layer coating film. When 0.1 μm of the silicon oxide film positioned under the opening portion of the resist underlayer film was removed, the etching treatment was stopped.

Then, in the resist underlayer film pattern left on the substrate, the shape of a line-and-space pattern, as generally referred to, in which substantially straight lines were arranged at regular intervals, was observed by an SEM (scanning electron microscope). In this line-and-space pattern, 100 substantially straight lines were arranged at regular intervals, with repeating constant intervals of 84 nm, and this assembly was regarded as one set. On one substrate, 21 sets of the pattern having different line widths were included, with the line widths varying by 1 nm from 50 nm to 30 nm. The line width as referred to herein means the width of one substantially straight line among lines arranged at regular intervals formed with the resist underlayer film. In the pattern of the same configuration on the substrate, the state of the pattern having each line width at arbitrary five points was observed by the SEM. Evaluation on the resistance to curving was made based on the results of the observation. The resistance to curving was evaluated as being: "A" (favorable) in a case where all the sidewalls of the patterned lines formed of the resist underlayer film stood straight; and "B" (unfavorable) in a case where at least one curved sidewall was found.

TABLE 2

| | Composition | Solubility in PGMEA | Refractive index | Extinction coefficient | Etching resistance | Heat resistance (%) | Flatness |
|---|---|---|---|---|---|---|---|
| Example 19 | J1-1 | A | 1.35 | 0.57 | 0.94 | 15 | A |
| Example 20 | J1-2 | A | 1.33 | 0.48 | 0.90 | 14 | A |
| Example 21 | J1-3 | A | 1.35 | 0.70 | 0.92 | 13 | A |
| Example 22 | J1-4 | A | 1.33 | 0.42 | 0.88 | 14 | A |
| Example 23 | J1-5 | A | 1.38 | 0.63 | 0.92 | 16 | A |
| Example 24 | J1-6 | A | 1.34 | 0.56 | 0.94 | 16 | A |
| Example 25 | J1-7 | A | 1.35 | 0.58 | 0.93 | 15 | A |
| Example 26 | J1-8 | A | 1.33 | 0.49 | 0.89 | 14 | A |
| Example 27 | J1-9 | A | 1.34 | 0.51 | 0.88 | 13 | A |
| Example 28 | J2-1 | A | 1.40 | 0.73 | 0.90 | 11 | B |
| Example 29 | J2-2 | A | 1.42 | 0.62 | 0.85 | 8 | B |
| Example 30 | J2-3 | A | 1.43 | 0.76 | 0.92 | 12 | B |
| Example 31 | J2-4 | A | 1.42 | 0.58 | 0.89 | 10 | B |
| Example 32 | J2-5 | A | 1.41 | 0.72 | 0.94 | 13 | B |
| Example 33 | J2-6 | A | 1.40 | 0.73 | 0.96 | 12 | B |
| Example 34 | J2-7 | A | 1.40 | 0.72 | 0.89 | 12 | B |
| Example 35 | J2-8 | A | 1.41 | 0.75 | 0.88 | 11 | B |
| Comparative Example 1 | CJ2-1 | B | 1.40 | 0.71 | 0.92 | 12 | C |
| Comparative Example 2 | CJ2-2 | B | 1.40 | 0.40 | 1 | 20 | C |

TABLE 3

| | Composition | Refractive index | Extinction coefficient | Etching resistance | Heat resistance (%) | Solvent resistance | Resistance to curving | Solubility in PGMEA | Coating property | Flatness |
|---|---|---|---|---|---|---|---|---|---|---|
| Example 36 | J2-9 | 1.31 | 0.49 | 0.88 | 7 | A | A | A | A | A |
| Example 37 | J2-10 | 1.33 | 0.48 | 0.89 | 10 | A | A | A | A | A |
| Example 38 | J2-11 | 1.37 | 0.56 | 0.90 | 9 | A | A | A | A | A |
| Example 39 | J2-12 | 1.38 | 0.58 | 0.91 | 13 | A | A | A | A | A |
| Example 40 | J2-13 | 1.36 | 0.55 | 0.86 | 12 | A | A | A | A | A |
| Example 41 | J2-14 | 1.34 | 0.49 | 0.88 | 12 | A | A | A | A | A |
| Example 42 | J2-15 | 1.39 | 0.68 | 0.89 | 8 | A | A | A | A | A |
| Comparative Example 3 | CJ2-3 | 1.40 | 0.40 | 1 | 20 | C | B | B | B | C |

As is clear from Table 2, the films formed from the compositions of Examples 19 to 35 had satisfactory characteristics on the refractive index, the extinction coefficient and the etching resistance, and as compared with the films formed from the compositions of Comparative Examples, had superior heat resistance and superior flatness.

In addition, as is clear from Table 3, the films formed from the compositions of Examples 36 to 42 had favorable refractive index and extinction coefficient and was superior in etching resistance, and as compared with the films formed from the compositions of Comparative Examples, had superior heat resistance. Moreover, the solvent resistance and the resistance to curving of the film formed were also favorable.

Formation of Films

Synthesis of Polymers

Example 43

Synthesis of Polymer (A2-14)

Into a 3 L four-neck flask, 77.103 g (250 mmol) of the compound (M-1) and 35.123 g (252.5 mmol) of the compound (M-3), as well as 69.105 g (500 mmol) of potassium carbonate as the alkali metal compound, and 240 g of N,N-dimethylacetamide (DMAc) and 50 g of toluene as the solvent were charged. Subsequently, the four-neck flask was equipped with a thermometer, a stirrer, a T-shape-stopcock having a nitrogen inlet tube, a Dean-Stark tube and a condenser.

Then, the flask was purged with nitrogen, and thereafter a reaction was allowed in the resulting solution at 130° C. for 8 hrs. After the mixture was cooled to room temperature (25° C.), the produced salt was removed with a filter paper, and the filtrate was placed into methanol to permit reprecipitation, followed by filtration to isolate the residue. The residue thus obtained was dried in vacuo at 60° C. overnight to obtain a white powder polymer (A2-14) which is a random copolymer having a structure represented by the following formula (P-9) (yielding amount: 97.11 g; yield: 95%). The polymer (A2-14) had an Mw of 112,000.

Synthesis Example 8

Synthesis of Polymer (a2-3)

In a similar manner to Example 19 except that 87.603 g (250 mmol) of the compound (M-9) and 35.123 g (252.5 mol) of the compound (M-3) were used as the monomer compound, a white powder polymer (a2-3) which is a random copolymer having a structure represented by the following formula (p-1) was obtained (yielding amount: 108.21 g; yield: 96%). The polymer (a2-3) had an Mw of 95,000.

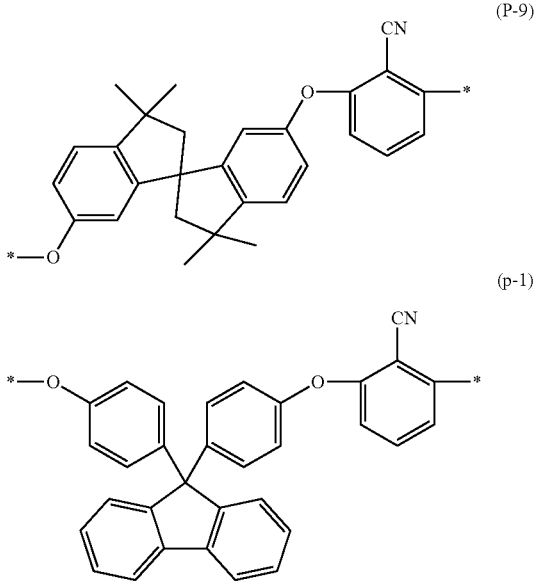

In the above formulae (P-9) and (p-1), * represents an atomic bonding.

Preparation of Composition and Formation of Film

Example 44

The polymer (A2-14) obtained as described above was redissolved in DMAc to obtain a composition (J2-16) having a polymer concentration of 20% by mass. The composition (J2-16) was applied on a substrate constituted with polyethylene terephthalate (PET) using a doctor blade, and dried at 70° C. for 30 min, then further dried at 100° C. for 30 min to give a film. The film was then separated from the PET substrate. Thereafter, the film was fixed to a metal frame, and further dried at 230° C. for 2 hrs to obtain a film having a thickness of 30 μm. Physical properties of the obtained film are shown together in Table 4.

Comparative Example 4

In a similar manner to Example 44 except that the resultant polymer (a2-3) was used, a composition (CJ2-4) was prepared, and a film was obtained by using the composition (CJ2-4).
Evaluations
(1) Optical Characteristics
Total Light Transmittance (Tt), Haze, YI Value
The total light transmittance (%), the haze (%) and the YI value were determined on the film obtained as described above according to JIS K7105, a test method of transparency. Specifically, the total light transmittance and the haze of the film were determined by using a haze meter, model SC-3H manufactured by Suga Test Instruments Co., Ltd., and the YI value was determined by using a Color Meter, model SM-T manufactured by Suga Test Instruments Co., Ltd.
Refractive Index
The refractive index of the film obtained as described above was determined by using a Multi-Wavelength Abbe Refractometer, model DR-M2 manufactured by Atago Co., Ltd. It is to be noted that the refractive index was measured at a wavelength of 589 nm
(2) Thermal Characteristics
Glass Transition Temperature (Tg)
The glass transition temperature (° C.) of the polymer obtained as described above was determined by using a Differential Scanning calorimeter (DSC), model 8230 manufactured by Rigaku Denki Co., at rate of temperature rise of 20° C./min.
Thermal Decomposition Temperature ($Td_5$)
The thermal decomposition temperature $Td_5$ of the polymer obtained as described above was determined by a thermogravimetric analysis (TGA: in nitrogen atmosphere, rate of temperature rise: 10° C./min; 5% weight loss temperature).
Coefficient of Linear Thermal Expansion (CTE)
The coefficient of linear thermal expansion of the film obtained as described above was determined by using a thermal mechanical analyzer, TMA model SSC-5200 manufactured by Seiko Instruments. After the temperature was elevated from the room temperature to 280° C., the temperature was lowered at a rate of 3° C./min, and the coefficient of linear thermal expansion was calculated from the slope in the range of from 200° C. to 100° C.

TABLE 4

| | | | Optical characteristics | | | | Thermal characteristics | | |
|---|---|---|---|---|---|---|---|---|---|
| | | | total light transmittance (%) | haze (%) | YI value | refractive index | Tg (° C.) | $Td_5$ (° C.) | coefficient of linear thermal expansion (ppm/K) |
| | Composition | Polymer | | | | | | | |
| Example 44 | J2-16 | A2-14 | 90 | 0.2 | 1.8 | 1.598 | 223 | 479 | 63 |
| Comparative Example 4 | CJ2-4 | a2-3 | 88 | 0.3 | 1.4 | 1.665 | 282 | 551 | 61 |

As is proven from the results shown in Table 4, the compositions and polymers of Examples enable formation of a film that is superior in both the optical characteristics such as transparency, and the thermal characteristics such as heat resistance.

In the composition according to the embodiment of the present invention, PGMEA may be used as a solvent, and the composition is capable of forming a film that is superior in heat resistance and flatness while general characteristics such as etching resistance are maintained. The method for producing a patterned substrate according to another embodiment of the present invention enables a resist underlayer film that is superior in heat resistance and flatness to be readily formed owing to superior coating properties, and in turn, enables a favorable pattern to be formed. The film according to the still other embodiment of the present invention is superior in both the optical characteristics such as transparency, and the thermal characteristics such as heat resistance. According to the method for forming a film of the yet another embodiment of the present invention, the film as described above can be readily formed. The compound according to the other embodiment of the present invention can be suitably used as a component of the composition described above. Therefore, these can be suitably used in, for example, production of semiconductor devices, and the like, in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A composition comprising:
a compound represented by formula (2); and
a solvent:

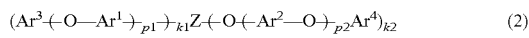
(2)

wherein, in the formula (2), Z is a partial structure represented by formula (1); k1 and k2 are each independently an integer of 1 to 8, wherein a sum of k1 and k2 is no less than 3 and no greater than 16; $Ar^1$ and $Ar^2$ each independently represent a substituted or unsubstituted arenediyl group having 6 to 15 ring atoms; p1 and p2 are each independently an integer of 1 to 3; and $Ar^3$ and $Ar^4$ each independently represent a substituted or unsubstituted aryl group having 6 to 15 ring atoms, wherein in a case where $Ar^1$ to $Ar^4$, p1 and p2 are each present in a plurality of number, the plurality of $Ar^1$s are each identical or different, the plurality of $Ar^2$s are each identical or different, the plurality of $Ar^3$s are each identical or different, the plurality of $Ar^4$s are each identical or different, the plurality of p1s are each identical or different and the plurality of p2s are each identical or different,

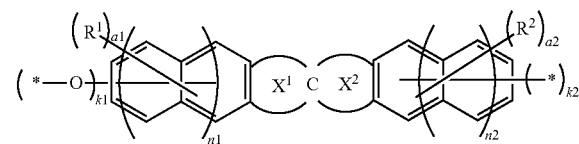
(1)

wherein, in the formula (1), $X^1$ and $X^2$ each independently represent a substituted or unsubstituted ring structure having 4 to 10 ring atoms constituted taken together with the spiro carbon atom and the carbon atoms of the aromatic ring adjacent to $X^1$ or $X^2$; $R^1$ and $R^2$ each independently represent a halogen atom, a nitro group or a monovalent organic group; a1 and a2 are each independently an integer of 0 to 7, wherein in a case where $R^1$ and $R^2$ are each present in a plurality of number, the plurality of $R^1$s are each identical or different, and the plurality of $R^2$s are each identical or different; n1 and n2 are each independently an integer of 0 to 2; k1 and k2 are each as defined in the formula (2), a sum of a1 and k1, and a sum of a2 and k2 are each no less than 1 and no greater than 8; and * represents an atomic bonding.

2. The composition according to claim 1, wherein the solvent comprises a polyhydric alcohol partial ether acetate solvent, a ketone solvent, a carboxylic acid ester solvent, or a combination thereof.

3. A method for producing a patterned substrate, comprising:
applying a composition on an upper face side of a substrate to provide a resist underlayer film;
forming a resist pattern directly or indirectly on the resist underlayer film; and
etching at least the resist underlayer film and the substrate using the resist pattern as a mask such that the substrate has a pattern,
wherein the composition comprises:
a compound represented by formula (2); and
a solvent:

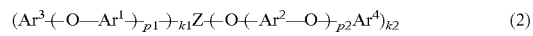
(2)

wherein, in the formula (2), Z is a partial structure represented by formula (1); k1 and k2 are each independently an integer of 1 to 8, wherein a sum of k1 and k2 is no less than 3 and no greater than 16; $Ar^1$ and $Ar^2$ each independently represent a substituted or unsubstituted arenediyl group having 6 to 15 ring atoms; p1 and p2 are each independently an integer of 1 to 3; and $Ar^3$ and $Ar^4$ each independently represent a substituted or unsubstituted aryl group having 6 to 15 ring atoms, wherein in a case where $Ar^1$ to $Ar^4$, p1 and p2 are each present in a plurality of number, the plurality of $Ar^1$s are each identical or different, the plurality of $Ar^2$s are each identical or different, the plurality of $Ar^3$s are each identical or different, the plurality of $Ar^4$s are each identical or different, the plurality of p1s are each identical or different and the plurality of p2s are each identical or different,

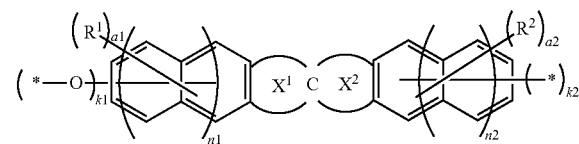
(1)

wherein, in the formula (1), $X^1$ and $X^2$ each independently represent a substituted or unsubstituted ring structure having 4 to 10 ring atoms constituted taken together with the spiro carbon atom and the carbon atoms of the aromatic ring adjacent to $X^1$ or $X^2$; $R^1$ and $R^2$ each independently represent a halogen atom, a nitro group or a monovalent organic group; a1 and a2 are each independently an integer of 0 to 7, wherein in a case where $R^1$ and $R^2$ are each present in a plurality of number, the plurality of $R^1$s are each identical or different, and the plurality of $R^2$s are each identical or different; n1 and n2 are each independently an integer of 0 to 2; k1 and k2 are each as defined in the formula (2), wherein a sum of a1 and k1, and a sum of a2 and k2 are each no less than 1 and no greater than 8; and * represents an atomic bonding.

4. A method for forming a film, comprising:
providing a coating film using a composition; and
removing a solvent from the coating film,
wherein the composition comprises:
a compound represented by formula (2); and
the solvent:

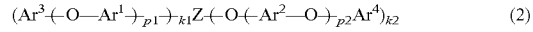
(2)

wherein, in the formula (2), Z is a partial structure represented by formula (1); k1 and k2 are each independently an integer of 1 to 8, wherein a sum of k1 and k2 is no less than 3; p1 and p2 are each independently an integer of 1 to 3; and $Ar^3$ and $Ar^4$ each independently represent a substituted or unsubstituted aryl group having 6 to 15 ring atoms, wherein in a case where $Ar^1$ to $Ar^4$, p1 and p2 are each present in a plurality of number, the plurality of $Ar^3$s are each identical or different, the plurality of $Ar^2$s are each identical or different, the plurality of $Ar^3$s are each identical or different, the plurality of $Ar^4$s are each identical or different, the plurality of p1s are each identical or different and the plurality of p2s are each identical or different,

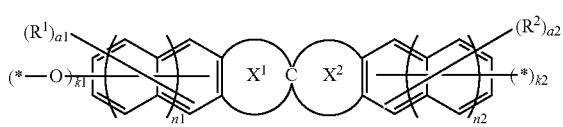

(1)

wherein, in the formula (1), $X^1$ and $X^2$ each independently represent a substituted or unsubstituted ring structure having 4 to 10 ring atoms constituted taken together with the spiro carbon atom and the carbon atoms of the aromatic ring adjacent to $X^1$ or $X^2$; $R^1$ and $R^2$ each independently represent a halogen atom, a nitro group or a monovalent organic group; a1 and a2 are each independently an integer of 0 to 7, wherein in a case where $R^1$ and $R^2$ are each present in a plurality of number, the plurality of $R^1$s are each identical or different, and the plurality of $R^2$s are each identical or different; n1 and n2 are each independently an integer of 0 to 2; k1 and k2 are each as defined in the formula (2), wherein a sum of a1 and k1, and a sum of a2 and k2 are each no less than 1 and no greater than 8; and * represents an atomic bonding.

5. The method according to claim 3, wherein the solvent comprises a polyhydric alcohol partial ether acetate solvent, a ketone solvent, a carboxylic acid ester solvent, or a combination thereof.

6. The method according to claim 3, wherein in the formula (2), p1 and p2 are each independently an integer of 1 or 2.

7. The method according to claim 3, wherein in the formula (2), p1 and p2 are each an integer of 1.

8. The method according to claim 7, wherein in the formula (2), each of $Ar^1$ and $Ar^2$ is substituted with a cyano group.

9. The method according to claim 3, wherein in the formula (2), at least one of $Ar^1$, $Ar^2$, $Ar^3$, and $Ar^4$ is substituted with a fluorine atom, a chlorine atom, a bromine atom, an iodine atom, a hydroxy group, an amino group, a cyano group, a nitro group, an alkoxy group, an alkoxycarbonyl group, an alkoxycarbonyloxy group, an acyl group, an arylaminocarbonyl group, or an arylamino group.

10. The method according to claim 3, wherein in the formula (2), at least one of $Ar^1$, $Ar^2$, $Ar^3$, and $Ar^4$ is substituted with a cyano group.

11. The method according to claim 3, wherein the composition further comprises an acid generating agent.

12. The method according to claim 3, wherein the composition further comprises a crosslinking agent.

13. The method according to claim 4, wherein in the formula (2), p1 and p2 are each independently an integer of 1 or 2.

14. The method according to claim 4, wherein in the formula (2), p1 and p2 are each an integer of 1.

15. The method according to claim 14, wherein in the formula (2), each of $Ar^1$ and $Ar^2$ is substituted with a cyano group.

16. The method according to claim 4, wherein in the formula (2), at least one of $Ar^1$, $Ar^2$, $Ar^3$, and $Ar^4$ is substituted with a fluorine atom, a chlorine atom, a bromine atom, an iodine atom, a hydroxy group, an amino group, a cyano group, a nitro group, an alkoxy group, an alkoxcarbonyl group, an alkoxycarbonyloxy group, an acyl group, an arylaminocarbonyl group, or an arylamino group.

17. The method according to claim 4, wherein in the formula (2), at least one of $Ar^1$, $Ar^2$, $Ar^3$, and $Ar^4$ is substituted with a cyano group.

18. The method according to claim 4, wherein the composition further comprises an acid generating agent.

19. The method according to claim 4, wherein the composition further comprises a crosslinking agent.

20. The composition according to claim 1, wherein in the formula (2), p1 and p2 are each an integer of 1.

21. The composition according to claim 20, wherein in the formula (2), each of $Ar^1$ and $Ar^2$ is substituted with a cyano group.

* * * * *